United States Patent
Kamtekar et al.

(10) Patent No.: US 9,812,644 B2
(45) Date of Patent: Nov. 7, 2017

(54) COMPOSITION CONTAINING DOPANT AND CO-POLYMERS HAVING NON-CONJUGATED SPACER UNITS AND ITS USE IN OLED DEVICES

(71) Applicants: Cambridge Display Technology, Cambridgeshire (GB); Sumitomo Chemical Company Limited, Tokyo (JP)

(72) Inventors: Kiran Kamtekar, Godmanchester (GB); Annette Steudel, Dresden (DE)

(73) Assignees: Cambridge Display Technology Limited, Cambridgeshire (GB); Sumitomo Chemical Company Limited, Tokyo (JP)

( * ) Notice: Subject to any disclaimer, the term of this patent is extended or adjusted under 35 U.S.C. 154(b) by 867 days.

(21) Appl. No.: 14/091,163

(22) Filed: Nov. 26, 2013

(65) Prior Publication Data

US 2014/0151660 A1    Jun. 5, 2014

(30) Foreign Application Priority Data

Nov. 30, 2012    (GB) .................................. 1221624.8

(51) Int. Cl.
*H01L 51/00*    (2006.01)
*C07F 5/02*    (2006.01)
(Continued)

(52) U.S. Cl.
CPC .......... *H01L 51/0043* (2013.01); *C07F 5/025* (2013.01); *C08G 61/02* (2013.01);
(Continued)

(58) Field of Classification Search
None
See application file for complete search history.

(56) References Cited

U.S. PATENT DOCUMENTS

2002/0038998 A1* 4/2002 Fujita ................... G09G 3/3233
                                                    313/495
2002/0113545 A1* 8/2002 Adachi ............... H01L 51/5016
                                                    313/504
(Continued)

FOREIGN PATENT DOCUMENTS

EP         1253180 A2    10/2002
JP         11-30873 A     2/1999
(Continued)

OTHER PUBLICATIONS

Yu et al., Synthesis of blue light emitting copolymers by oxidative coupling reaction, Synthetic Metals, 135-136, 2003, 201-202.*
(Continued)

*Primary Examiner* — Francisco Tschen
(74) *Attorney, Agent, or Firm* — Wolf, Greenfield & Sacks, P.C.

(57) ABSTRACT

A polymer comprising repeat units of formula (I) and one or more co-repeat units:

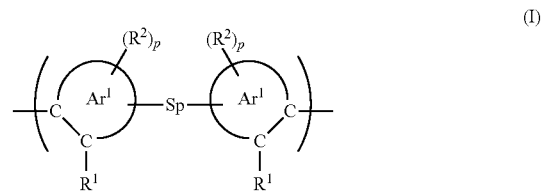

(I)

$Ar^1$ in each occurrence independently represent an aryl or heteroaryl group;
$R^1$ and $R^2$ in each occurrence independently represent a substituent;
p independently in each occurrence is 0 or a positive integer;
(Continued)

Sp represents a spacer group comprising at least one carbon or silicon atom spacing the two groups $Ar^1$ apart; and
each group $Ar^1$ is bound to an aromatic group of a co-repeat unit.

The polymer may form a charge-transporting layer of an OLED or may be a host material used with a luminescent dopant in a light-emitting layer of an OLED.

15 Claims, 1 Drawing Sheet

(51) Int. Cl.
| | |
|---|---|
| *C08G 61/02* | (2006.01) |
| *C08G 61/12* | (2006.01) |
| *C09D 165/00* | (2006.01) |
| *C08K 5/3472* | (2006.01) |
| *C08K 5/56* | (2006.01) |
| *C08L 65/00* | (2006.01) |
| *H01L 51/50* | (2006.01) |
| *H01L 51/56* | (2006.01) |

(52) U.S. Cl.
CPC ............ *C08G 61/12* (2013.01); *C08K 5/3472* (2013.01); *C08K 5/56* (2013.01); *C08L 65/00* (2013.01); *C09D 165/00* (2013.01); *H01L 51/50* (2013.01); *H01L 51/56* (2013.01); *C08G 2261/122* (2013.01); *C08G 2261/1412* (2013.01); *C08G 2261/19* (2013.01); *C08G 2261/3142* (2013.01); *C08G 2261/3162* (2013.01); *C08G 2261/3424* (2013.01); *C08G 2261/411* (2013.01); *C08G 2261/5242* (2013.01); *C08G 2261/76* (2013.01); *C08G 2261/95* (2013.01)

(56) References Cited

U.S. PATENT DOCUMENTS

2002/0177687 A1* 11/2002 Noguchi ................ C08G 61/02
 528/498
2006/0199943 A1* 9/2006 Falcou ................... C08G 61/02
 528/422
2008/0176104 A1* 7/2008 Towns ................ H01L 51/0035
 428/704

FOREIGN PATENT DOCUMENTS

| JP | 11-264981 A | 9/1999 |
| KR | 10-0811058 B1 | 3/2008 |
| WO | WO 2011/141714 A1 | 11/2011 |
| WO | WO 2012/048778 A1 | 4/2012 |

OTHER PUBLICATIONS

McGehee et al., Narrow Bandwidth Luminescence from Blends with Energy Transfer from Semiconducting Conjugated Polymers to Europium Complexes, Adv. Mater. 1999,11,16,1349-1354.*

Liao et al.,Efficient Blue-Green-Emitting Poly[(5-diphenylamino-1,3-phenylenevinylene)-alt-(2,5-dihexyloxy-1,4-phenylenevinylene)] Derivatives: Synthesis and Optical Properties; Journal of Polymer Science: Part A: Polymer Chemistry; 2006; 2307-2315.*

EP 13194928.1, Mar. 27, 2014, Extended European Search Report.

Remmers et al., Synthesis, optical absorption and fluorescence of new poly(p-phenylene)-related polymers. Macromolecular: Rapid Communications. 1996:17(4):239-52.

Yu et al, "Synthesis of blue light emitting copolymers by oxidative coupling reaction" Synthetic Metals, dated 2003, pp. 135-136, 201-202.

Combined Search Examination Report for corresponding GB Patent No. GB1221624.8, dated Mar. 25, 2013, pp. 1-6.

Li et al., Organic Light-Emitting Materials and Devices. Taylor & Francis, Boca Raton. 2007;436-7.

Examination Report mailed Nov. 16, 2016 for Application No. EP 13194928.1.

Liu et al., Role of Tetrakis(triphenylphosphine)palladium(0) in the Degradation and Optical Properties of Fluorene-Based Compounds. J Phys Chem C. 2008;112(27):10273-8.

* cited by examiner

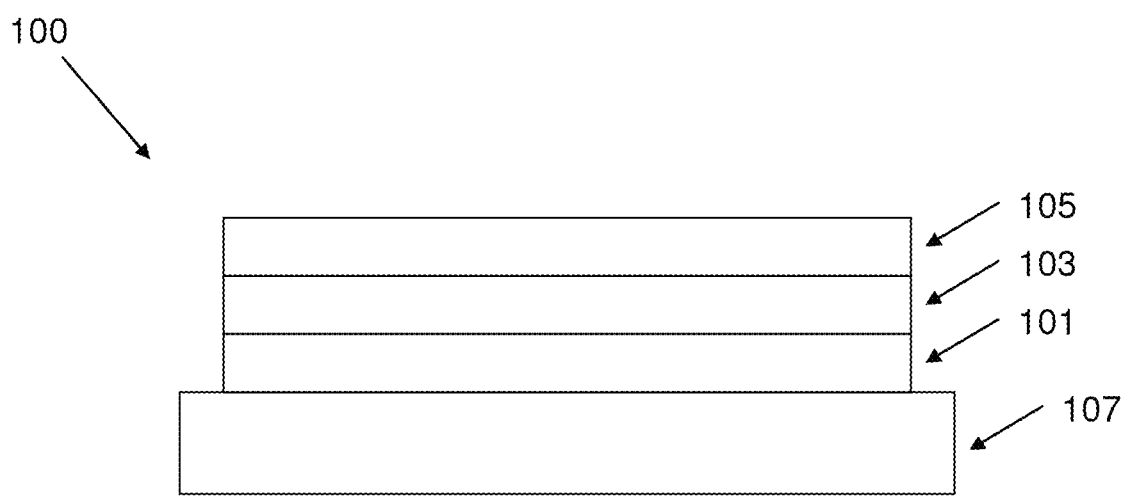

COMPOSITION CONTAINING DOPANT AND CO-POLYMERS HAVING NON-CONJUGATED SPACER UNITS AND ITS USE IN OLED DEVICES

RELATED APPLICATIONS

This application claims Foreign priority benefits under 35 U.S.C. §119(a)-(d) or 35 U.S.C. §365(b) of British application number 1221624.8, filed Nov. 30, 2012, the entirety of which is incorporated herein.

BACKGROUND OF THE INVENTION

Electronic devices containing active organic materials are attracting increasing attention for use in devices such as organic light emitting diodes (OLEDs), organic photoresponsive devices (in particular organic photovoltaic devices and organic photosensors), organic transistors and memory array devices. Devices containing active organic materials offer benefits such as low weight, low power consumption and flexibility. Moreover, use of soluble organic materials allows use of solution processing in device manufacture, for example inkjet printing or spin-coating.

An OLED may comprise a substrate carrying an anode, a cathode and one or more organic light-emitting layers between the anode and cathode.

Holes are injected into the device through the anode and electrons are injected through the cathode during operation of the device. Holes in the highest occupied molecular orbital (HOMO) and electrons in the lowest unoccupied molecular orbital (LUMO) of a light-emitting material combine to form an exciton that releases its energy as light.

A light emitting layer may comprise a semiconducting host material and a light-emitting dopant wherein energy is transferred from the host material to the light-emitting dopant. For example, J. Appl. Phys. 65, 3610, 1989 discloses a host material doped with a fluorescent light-emitting dopant (that is, a light-emitting material in which light is emitted via decay of a singlet exciton).

Phosphorescent dopants are also known (that is, a light-emitting dopant in which light is emitted via decay of a triplet exciton).

A hole-transporting layer may be provided between the anode and light-emitting layer of an OLED.

Suitable light-emitting materials include small molecule, polymeric and dendrimeric materials. Suitable light-emitting polymers include poly(arylene vinylenes) such as poly (p-phenylene vinylenes) and polymers containing arylene repeat units, such as fluorene repeat units. Blue light-emitting fluorene homopolymer is disclosed in WO 97/05184.

WO 00/53656 discloses a method of forming a conjugated polymer by reacting a monomer carrying halide reactive functional groups and a monomer carrying boron derivative reactive functional groups in the presence of a palladium catalyst.

WO 2005/013386 discloses an organic light-emitting device comprising a host polymer material and a luminescent metal complex wherein the polymer material may comprise non-planar repeat units or partially or fully non-conjugated repeat units in order to reduce conjugation of the polymer.

WO 2011/141709 discloses a light-emitting composition comprising a host polymer and a light-emitting dopant wherein the host polymer comprises conjugating repeat units and non-conjugating repeat units in a backbone of the polymer. The non-conjugating repeat units comprise an at least partially saturated ring having at least one ring atom that breaks any conjugation path between repeat units linked to the non-conjugating repeat units.

WO 2010/085676 discloses host materials for electrophosphorescent devices. A copolymer formed by copolymerization of 1,6-bis(3-(4,4,5,5-tetramethyl-[1,3,2]-dioxaborolan-2-yl)phenoxyl)hexane and 2-(4-(3-(3,6-dibromocarbazol-9-yl)propyl)phenyl)-4,6-di(3-methylphenyl)-1,3,5-triazine is disclosed.

JP 2005/158561 discloses non-conjugated polymers containing an electron transporting compound.

US 2011/095269 discloses the following polymer:

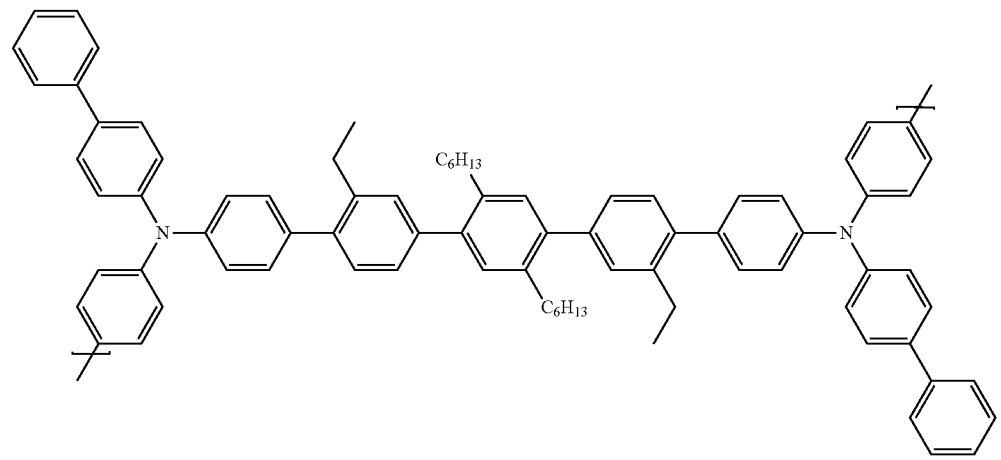

WO 2012/048778 discloses polymers formed by polymerization of the following monomers:

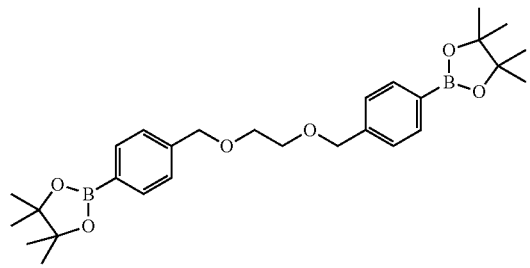

50% (M2)

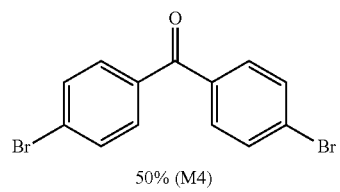

50% (M4)

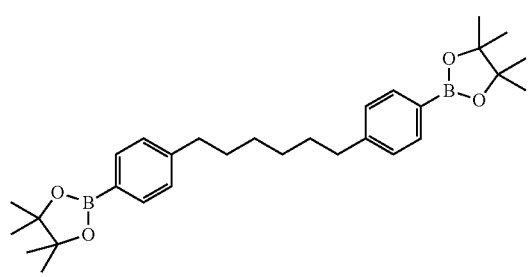

50% (M3)

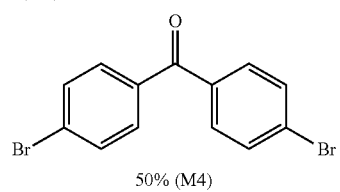

50% (M4)

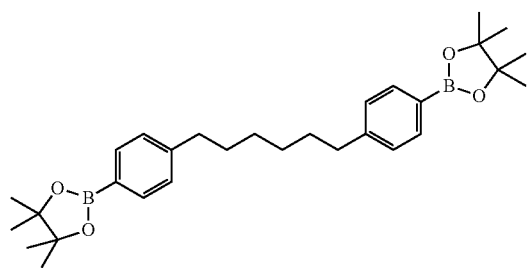

50% (M3)

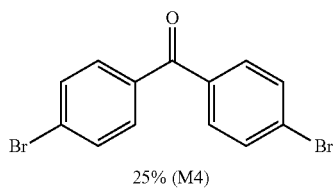

25% (M4)

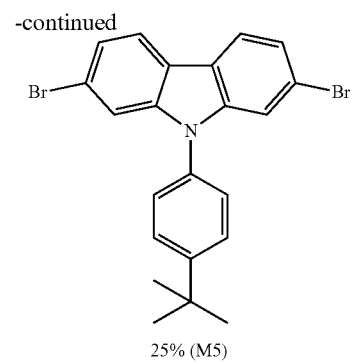

25% (M5)

U.S. Pat. No. 7,898,163 discloses a monomer having the following formula:

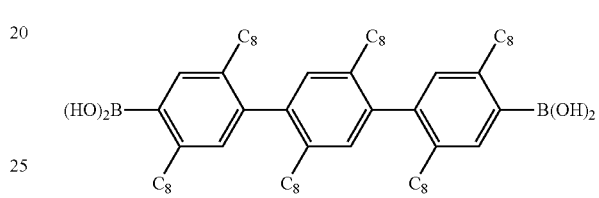

SUMMARY OF THE INVENTION

In a first aspect the invention provides a polymer comprising repeat units of formula (I) and one or more co-repeat units:

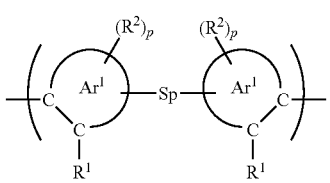

(I)

wherein $Ar^1$ in each occurrence independently represents an aryl or heteroaryl group;
$R^1$ and $R^2$ in each occurrence independently represent a substituent;
p independently in each occurrence is 0 or a positive integer;
Sp represents a spacer group comprising at least one carbon or silicon atom spacing the two groups $Ar^1$ apart; and
each group $Ar^1$ is bound to an aromatic group of a co-repeat unit.

In a second aspect the invention provides a monomer of formula (Im):

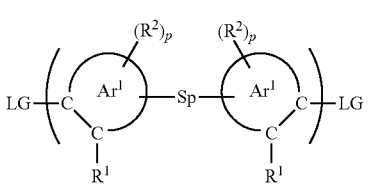

(Im)

wherein LG is a leaving group capable of leaving in a coupling reaction to form a carbon-carbon bond between $Ar^1$ and an aromatic or heteroaromatic group, and $Ar^1$, $R^1$, $R^2$, p and Sp are as described in the first aspect.

In a third aspect the invention provides a method of forming a polymer according to the first aspect, the method comprising the step of polymerising a monomer according to the second aspect and one or more co-monomers for forming the one or more respective co-repeat units.

In a fourth aspect the invention provides a composition comprising a polymer according to the first aspect and at least one light-emitting dopant.

In a fifth aspect the invention provides a formulation comprising a polymer according to the first aspect or a composition according to the fourth aspect and at least one solvent.

In a sixth aspect the invention provides an organic light-emitting device comprising an anode, a cathode and one or more organic layers between the anode and cathode including a light-emitting layer wherein at least one of the one or more organic layers comprises a polymer according to the first aspect.

In a seventh aspect the invention provides a method of forming an organic light-emitting device according to the sixth aspect, the method comprising the step of forming the light-emitting layer over one of the anode and the cathode and forming the other of the anode and the cathode over the light-emitting layer

DESCRIPTION OF THE DRAWINGS

The invention will now be described in more detail with reference to the drawings in which:

FIG. 1 illustrates an OLED according to an embodiment of the invention.

DETAILED DESCRIPTION OF THE INVENTION

FIG. 1 illustrates an OLED 100 according to an embodiment of the invention comprising an anode 101, a cathode 105 and a light-emitting layer 103 between the anode and cathode. The device 100 is supported on a substrate 107, for example a glass or plastic substrate.

One or more further layers may be provided between the anode 101 and cathode 105, for example hole-transporting layers, electron transporting layers, hole blocking layers and electron blocking layers. The device may contain more than one light-emitting layer.

Preferred device structures include:
Anode/Hole-injection layer/Light-emitting layer/Cathode
Anode/Hole transporting layer/Light-emitting layer/Cathode
Anode/Hole-injection layer/Hole-transporting layer/Light-emitting layer/Cathode
Anode/Hole-injection layer/Hole-transporting layer/Light-emitting layer/Electron-transporting layer/Cathode.

Preferably, at least one of a hole-transporting layer and hole injection layer is present. Preferably, both a hole injection layer and hole-transporting layer are present.

Light-emitting materials include red, green and blue light-emitting materials.

A blue emitting material may have a photoluminescent spectrum with a peak in the range of 400-490 nm, optionally 420-490 nm.

A green emitting material may have a photoluminescent spectrum with a peak in the range of more than 490 nm up to 580 nm, optionally more than 490 nm up to 540 nm.

A red emitting material may optionally have a peak in its photoluminescent spectrum of more than 580 nm up to 630 nm, optionally 585-625 nm.

Light-emitting layer 103 may contain a polymer of the invention. The polymer may be doped with one or more luminescent dopants. The light-emitting layer 103 may consist essentially of the polymer and the one or more luminescent dopants, or may contain one or more further materials, for example one or more charge-transporting materials or one or more further light-emitting materials. When used as a host material for one or more light-emitting dopants, the singlet or triplet energy level of the host material is preferably no more than 0.1 eV below that of the light-emitting material, and is more preferably about the same or higher than that of the light-emitting material in order to avoid quenching of luminescence from the light-emitting dopant.

In a preferred embodiment, light-emitting layer 103 contains a polymer of the invention and at least one of green and blue phosphorescent light-emitting materials.

A charge-transporting layer adjacent to a phosphorescent light-emitting layer preferably contains a charge-transporting material having a $T_1$ excited state energy level that is no more than 0.1 eV lower than, preferably the same as or higher than, the $T_1$ excited state energy level of the phosphorescent light-emitting material(s) of the invention in order to avoid quenching of triplet excitons migrating from the light-emitting layer into the charge-transporting layer. Accordingly, a polymer of the invention may be used as a charge-transporting material in a charge-transporting layer. In one preferred arrangement, a hole-transporting layer comprises or consists essentially of the polymer.

Triplet energy levels may be measured from the energy onset of the phosphorescence spectrum measured by low temperature phosphorescence spectroscopy (Y. V. Romaovskii et al, Physical Review Letters, 2000, 85 (5), p 1027, A. van Dijken et al, Journal of the American Chemical Society, 2004, 126, p 7718).

The polymer contains non-conjugating repeat units of formula (I)

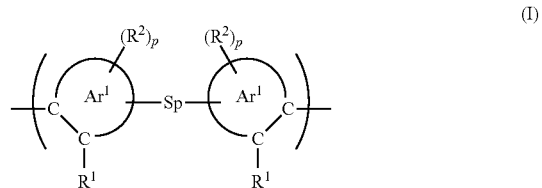

The repeat units of formula (I) contain aromatic or heteroaromatic groups $Ar^1$ spaced apart by a spacer group Sp. The spacer group does not provide any conjugation path between the two groups $Ar^1$, and therefore does not provide any conjugation path between repeat units on either side of the non-conjugating repeat units of formula (I).

However the groups $Ar^1$ are capable of conjugating to aromatic or heteroaromatic groups of repeat units adjacent to the repeat unit of formula (I). The present inventors have found that even this relatively limited extent of conjugation between the repeat unit of formula (I) and an adjacent repeat unit can result in poor device performance, particularly when the polymer is used as a host for a dopant with a high excited state energy level, such as a phosphorescent green or blue light-emitting material.

Without wishing to be bound by any theory, it is believed that this poor device performance may be due to a reduction in singlet and triplet excited state energy levels upon conjugation. By providing substituents $R^1$ on the groups $Ar^1$ adjacent to the positions through which the repeat units of formula (I) are linked to adjacent repeat units, steric hindrance may be created between the groups $Ar^1$ and the aromatic groups bound of adjacent repeat units that are bound to $Ar^1$, creating a twist between repeat units of formula (I) and adjacent repeat units and reducing the extent of conjugation therebetween. The relatively high triplet excited state energy level may make the polymers of the invention suitable for use as hosts for phosphorescent light-emitting materials, including red, green and blue phosphorescent light-emitting materials, and/or as charge-transporting materials adjacent to light-emitting layers containing phosphorescent light-emitting materials The polystyrene-equivalent number-average molecular weight (Mn) measured by gel permeation chromatography of the polymers described herein may be in the range of about $1\times10^3$ to $1\times10^8$, and preferably $1\times10^4$ to $5\times10^6$. The polystyrene-equivalent weight-average molecular weight (Mw) of the polymers described herein may be $1\times10^3$ to $1\times10^8$, and preferably $1\times10^4$ to $1\times10^7$.

Polymers as described herein are suitably amorphous polymers.

Polymer Synthesis

Polymers as described herein may be formed by a polymerisation carried out in the presence of a metal catalyst.

One method of forming conjugated or partially conjugated polymers is Suzuki polymerisation, for example as described in WO 00/53656 or U.S. Pat. No. 5,777,070 which allows formation of C—C bonds between two aromatic or heteroaromatic groups, and so enables formation of polymers having conjugation extending across two or more repeat units. Suzuki polymerisation takes place in the presence of a palladium complex catalyst and a base.

As illustrated in Scheme 1, in the Suzuki polymerisation process a monomer for forming repeat units RU1 having leaving groups LG1 such as boronic acid or boronic ester groups undergoes polymerisation with a monomer for forming repeat units RU2 having leaving groups LG2 such as halogen, preferably bromine or iodine; sulfonic acid; or sulfonic ester to form a carbon-carbon bond between Arylene 1 and Arylene 2:

nLG1-RU1-LG1+nLG2-RU2-LG2→-(RU1-RU2)$_n$-  Scheme 1

Exemplary boronic esters have formula (IV):

(IV)

wherein $R^6$ in each occurrence is independently a $C_{1-20}$ alkyl group, * represents the point of attachment of the boronic ester to an aromatic ring of the monomer, and the two groups $R^6$ may be linked to form a ring. In a preferred embodiment, the two groups $R^6$ are linked to form the pinacol ester of boronic acid:

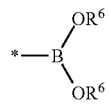

It will be understood by the skilled person that a monomer LG1-RU1-LG1 will not polymerise to form a direct carbon-carbon bond with another monomer LG1-RU1-LG1. A monomer LG2-RU2-LG2 will not polymerise to form a direct carbon-carbon bond with another monomer LG2-RU2-LG2.

Preferably, one of LG1 and LG2 is bromine or iodine and the other is a boronic acid or boronic ester.

This selectivity means that the ordering of repeat units in the polymer backbone can be controlled such that all or substantially all RU1 repeat units formed by polymerisation of LG1-RU1-LG1 are adjacent, on both sides, to RU2 repeat units.

In the example of Scheme 1 above, an AB copolymer is formed by copolymerisation of two monomers in a 1:1 ratio, however it will be appreciated that more than two or more than two monomers may be used in the polymerisation, and any ratio of monomers may be used.

The base may be an organic or inorganic base. Exemplary organic bases include tetra-alkylammonium hydroxides, carbonates and bicarbonates. Exemplary inorganic bases include metal (for example alkali or alkali earth) hydroxides, carbonates and bicarbonates.

The palladium complex catalyst may be a palladium (0) or palladium (II) compound.

Particularly preferred catalysts are tetrakis(triphenylphosphine)palladium (0) and palladium (II) acetate mixed with a phosphine.

A phosphine may be provided, either as a ligand of the palladium compound catalyst or as a separate compound added to the polymerisation mixture. Exemplary phosphines include triarylphosphines, for example triphenylphosphines wherein each phenyl may independently be unsubstituted or substituted with one or more substituents, for example one or more $C_{1-5}$ alkyl or $C_{1-5}$ alkoxy groups.

Particularly preferred are triphenylphospine and tris(ortho-methoxytriphenyl) phospine.

The polymerisation reaction may take place in a single organic liquid phase in which all components of the reaction mixture are soluble. The reaction may take place in a two-phase aqueous-organic system, in which case a phase transfer agent may be used. The reaction may take place in an emulsion formed by mixing a two-phase aqueous-organic system with an emulsifier.

The polymer may be end-capped by addition of an end-capping reactant. Suitable end-capping reactants are aromatic or heteroaromatic materials substituted with only one leaving group. The end-capping reactants may include reactants substituted with a halogen for reaction with a boronic acid or boronic ester group at a polymer chain end, and reactants substituted with a boronic acid or boronic ester for reaction with a halogen at a polymer chain end. Exemplary end-capping reactants are halobenzenes, for example bromobenzene, and phenylboronic acid. End-capping reactants may be added during or at the end of the polymerisation reaction.

Non-Conjugating Repeat Units $Ar^1$ of formula (I) is preferably an aryl group, more preferably phenylene. Phenylene groups $Ar^1$ may be 1,2-, 1,3- or 1,4-linked phenylene, preferably 1,4-linked phenylene.

Exemplary groups $R^1$ and (where present) $R^2$ include $C_{1-40}$ hydrocarbyl, $-OR^{11}$, $-SR^{11}$, $-NR^{11}{}_2$, and $-SiR^{11}{}_3$ wherein $R^{11}$ in each occurrence is a substituent, preferably $C_{1-40}$ hydrocarbyl.

Optionally, $R^1$ is a $C_{1-40}$ hydrocarbyl, which may the same or different in each occurrence.

Exemplary hydrocarbyl groups $R^1$, $R^2$ and $R^{11}$ include $C_{1-20}$ alkyl; unsubstituted phenyl; phenyl substituted with one or more $C_{1-20}$ alkyl groups; and a branched or linear chain of phenyl groups wherein each phenyl is unsubstituted or substituted with one or more $C_{1-20}$ alkyl groups. $C_{1-20}$ alkyl is preferred.

One or more non-adjacent C atoms of $R^1$ and, where present, $R^2$ may independently be replaced with $-O-$, $-S-$, $-NR_{11}-$, $-SiR_{11}{}^2-$, $C(=O)$ or $-COO-$.

Alkyl groups as described anywhere herein includes linear, branched and cyclic alkyl groups. In the case of $R^1$, a $C_{3-20}$ branched alkyl group, including alkyl groups containing one or more C atoms selected from secondary and tertiary carbon atoms, may provide more steric hindrance and therefore a greater degree of twisting than a corresponding linear alkyl group.

Sp of formula (I) is optionally a $C_{1-20}$ alkyl group wherein one or more non-adjacent C atoms of the alkyl group may be replaced with O, S, $-NR_{11}-$, $-SiR_{11}{}^2-$, $-C(=O)-$ or $-COO-$ and wherein $R^{11}$ in each occurrence is independently H or a substituent.

Sp of formula (I) may contain a single non-conjugating atom only between the two groups $Ar^1$, or Sp may contain non-conjugating chain of at least 2 atoms separating the two groups $Ar^1$.

A non-conjugating atom may be, for example, $-CR^4{}_2-$ or $-SiR^4{}_2-$ wherein $R^4$ in each occurrence is H or a substituent, optionally a substituent $R^{11}$ as described above, for example $C_{1-20}$ alkyl.

A spacer chain Sp may contain two or more atoms separating the two groups $Ar^1$, for example a $C_{1-20}$ alkyl chain wherein one or more non-adjacent C atoms of the chain may be replaced with O, S, $-NR_{11}-$, $-SiR_{11}{}^2-$, $-C(=O)-$ or $-COO-$. Preferably, the spacer chain Sp contains at least one $sp^3$-hybridised carbon atom separating the two groups $Ar^1$.

Preferred groups Sp are selected from $C_{1-20}$ alkyl wherein one or more non-adjacent C atoms are replaced with O. An oligo-ether chain, for example a chain of formula $-O(CH_2CH_2O)_n-$ may be provided, wherein n is from 1-5.

Repeat units of formula (I) may be provided in an amount in the range of 1-50 mol %, optionally 20-50 mol %. The polymer may contain two or more different repeat units of formula (I).

The repeat unit of formula (I) may have formula (Ia) or (Ib):

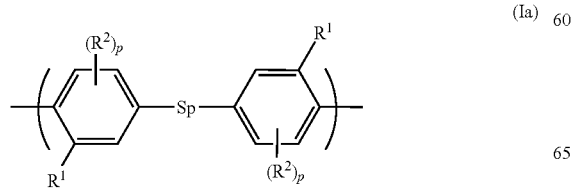
(Ia)

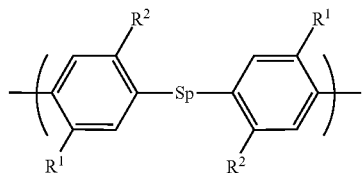
(Ib)

Exemplary repeat units of formula (I) include the following:

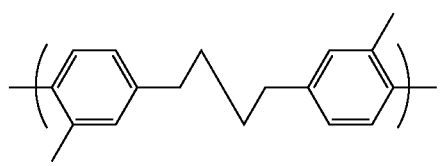

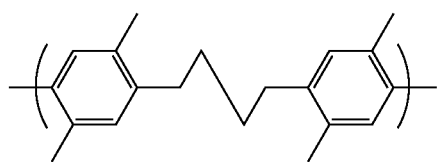

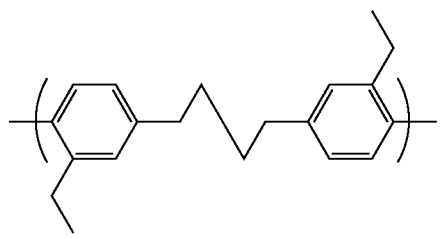

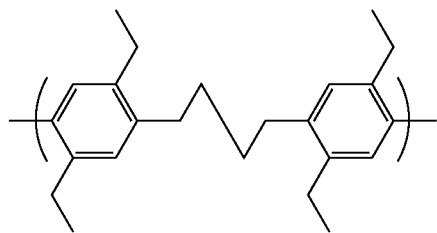

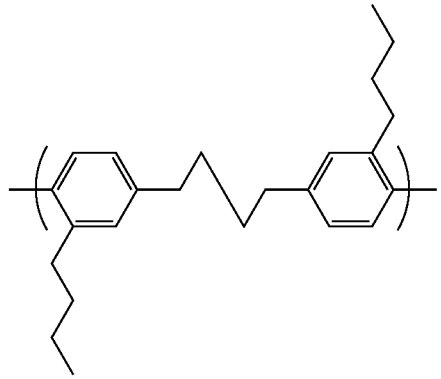

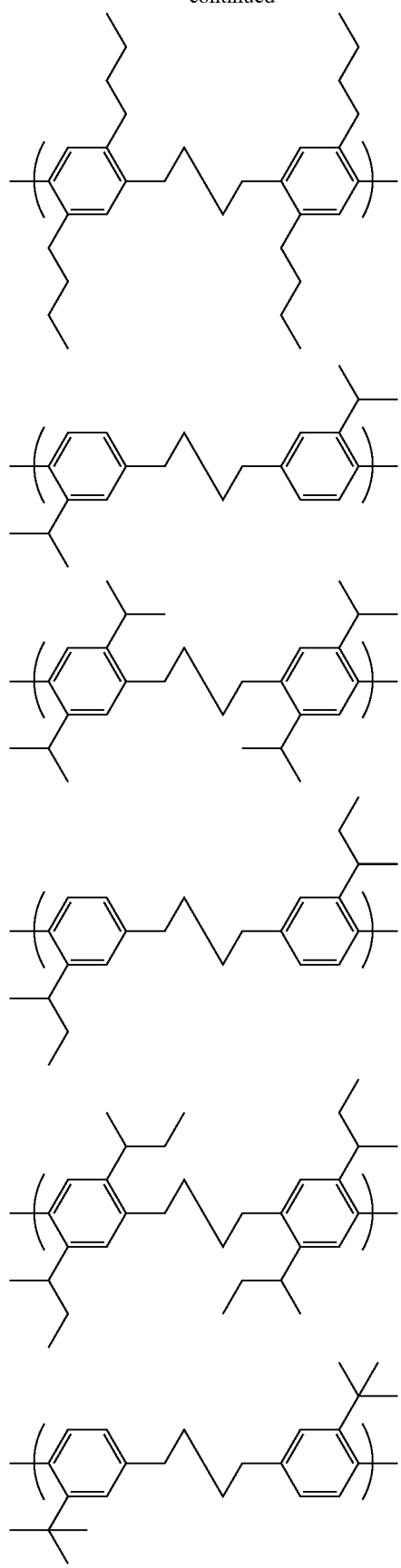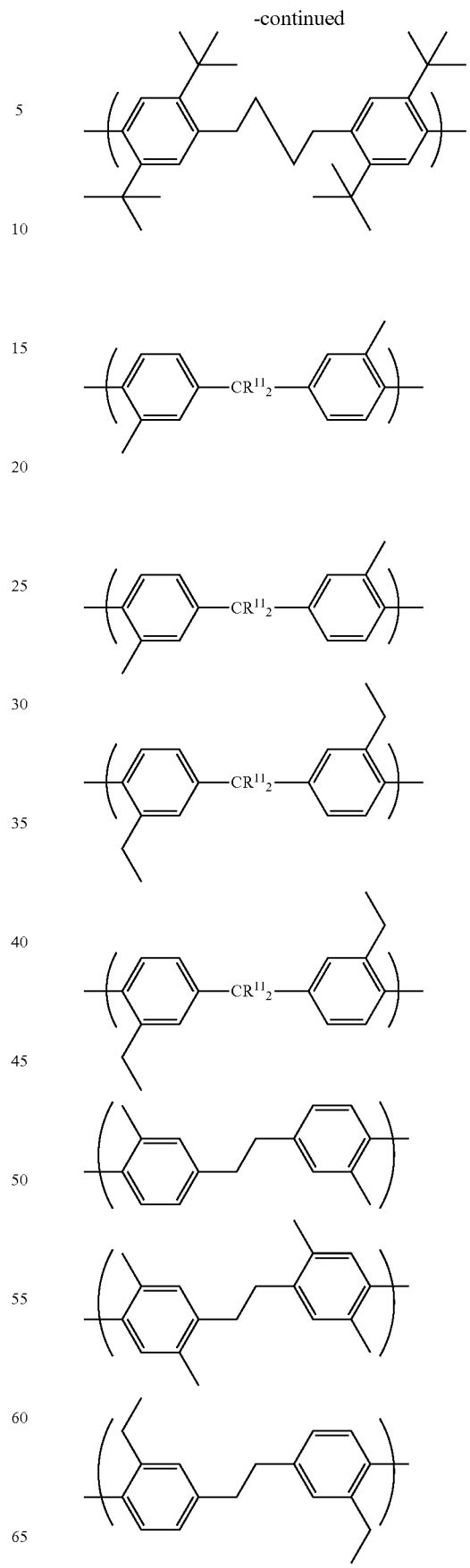

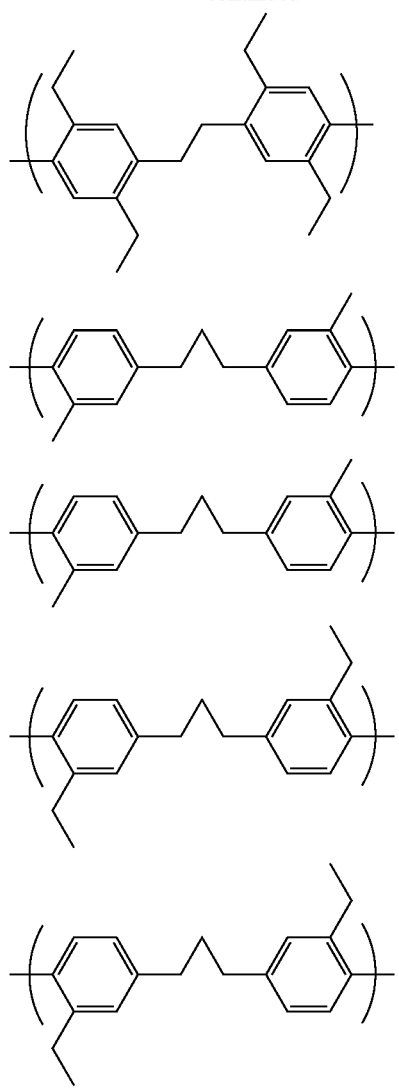
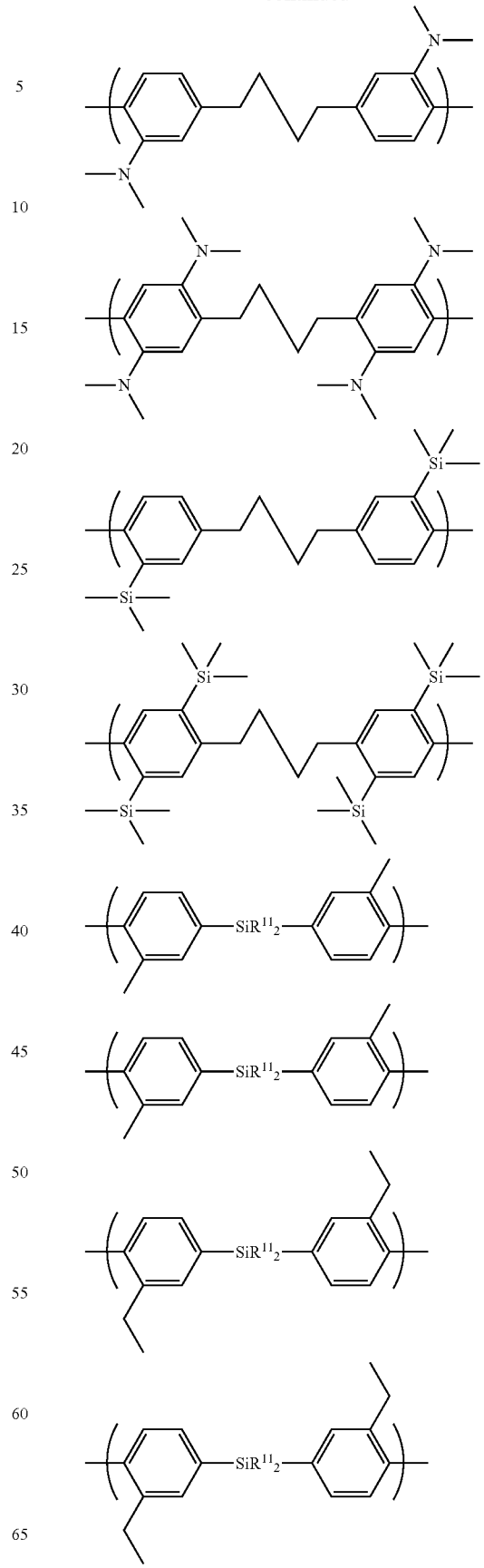
wherein $R^{11}$ in each occurrence is independently H or a substituent.
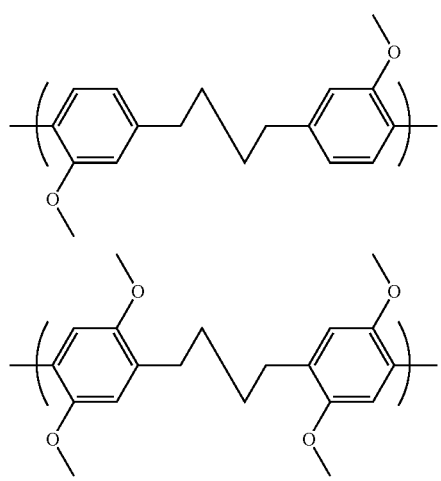

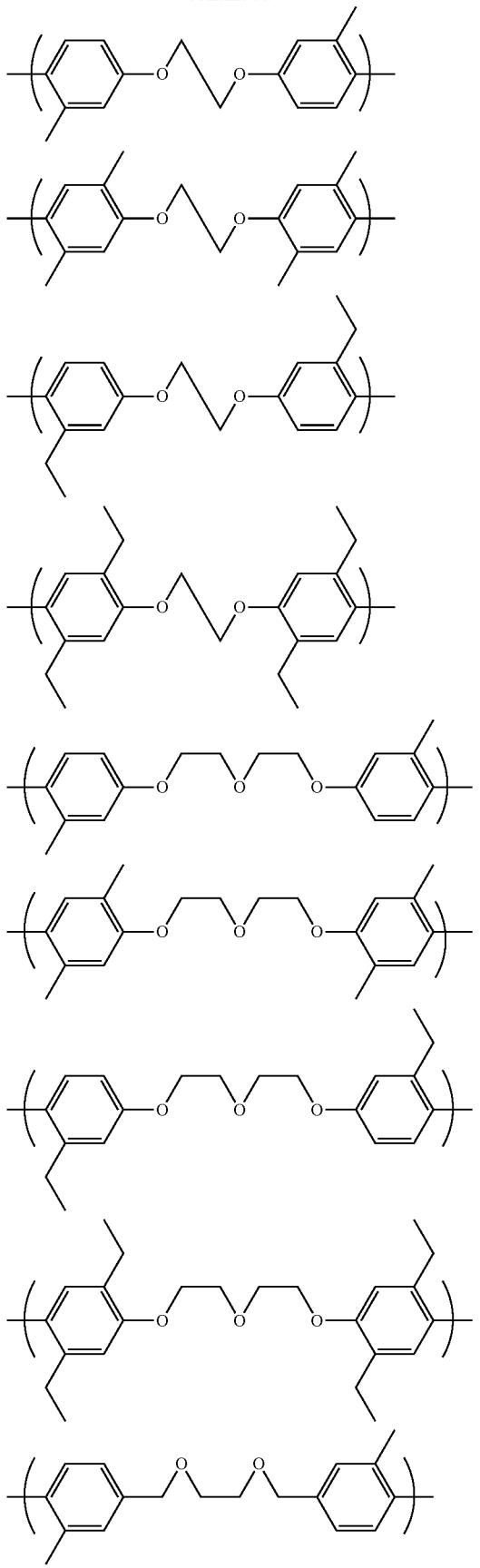

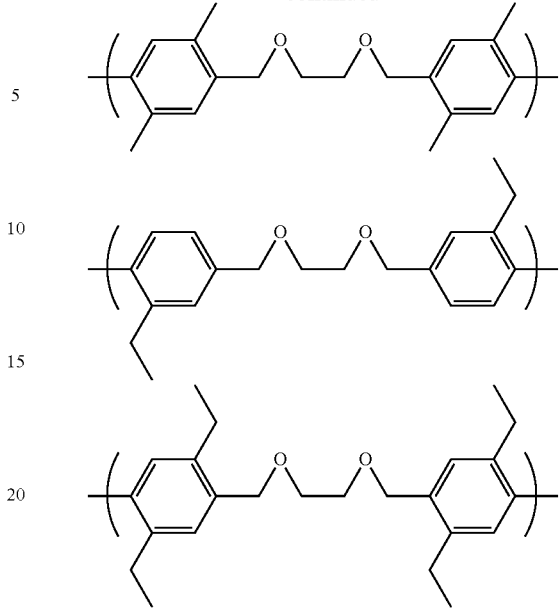

Co-Repeat Units

Polymers of the invention contain repeat units of formula (I) and one or more co-repeat units. Some or all of the co-repeat units contain an aromatic or heteroaromatic group that is bound to $Ar^1$ of repeat units of formula (I).

Exemplary co-repeat units include arylene or heteroarylene repeat units that may be unsubstituted or substituted with one or more substituents, and charge-transporting repeat units containing aromatic or heteroaromatic groups.

Co-repeat units include repeat units that may be directly adjacent to repeat units of formula (I) and repeat units that may be spaced apart from repeat units of formula (I). The copolymer may contain repeat units of formula (I) and adjacent co-repeat units only in the form of a regioregular AB copolymer of repeat units of formula (I) and adjacent co-repeat units, or it may contain repeat units of formula (I), co-repeat units adjacent to repeat units of formula (I), and one or more further co-repeat units Exemplary co-repeat units include arylene repeat units, for example 1,2-, 1,3- and 1,4-phenylene repeat units, 3,6- and 2,7-linked fluorene repeat units, indenofluorene, naphthalene, anthracene and phenanthrene repeat units, and stilbene repeat units, each of which may be unsubstituted or substituted with one or more substitutents, for example one or more $C_{1-30}$ hydrocarbyl substituents.

One preferred class of arylene repeat units is phenylene repeat units, such as phenylene repeat units of formula (III):

(III)

wherein q in each occurrence is independently 0, 1, 2, 3 or 4, optionally 1 or 2; n is 1, 2 or 3; and $R^3$ independently in each occurrence is a substituent.

Where present, each $R^3$ may independently be selected from the group consisting of:

alkyl, optionally $C_{1-20}$ alkyl, wherein one or more non-adjacent C atoms may be replaced with optionally substituted aryl or heteroaryl, O, S, substituted N, C=O or —COO—, and one or more H atoms may be replaced with F;

aryl and heteroaryl groups that may be unsubstituted or substituted with one or more substituents, preferably phenyl substituted with one or more $C_{1-20}$ alkyl groups;

a linear or branched chain of aryl or heteroaryl groups, each of which groups may independently be substituted, for example a group of formula —$(Ar^3)_r$ wherein each $Ar^3$ is independently an aryl or heteroaryl group and r is at least 2, preferably a branched or linear chain of phenyl groups each of which may be unsubstituted or substituted with one or more $C_{1-20}$ alkyl groups; and a crosslinkable-group, for example a group comprising a double bond such and a vinyl or acrylate group, or a benzocyclobutane group.

In the case where $R^3$ comprises an aryl or heteroaryl group, or a linear or branched chain of aryl or heteroaryl groups, the or each aryl or heteroaryl group may be substituted with one or more substituents $R^7$ selected from the group consisting of:

alkyl, for example $C_{1-20}$ alkyl, wherein one or more non-adjacent C atoms may be replaced with O, S, substituted N, C=O and —COO— and one or more H atoms of the alkyl group may be replaced with F;

$NR^9_2$, $OR^9$, $SR^9$, $SiR^9_3$ and fluorine, nitro and cyano;

wherein each $R^9$ is independently selected from the group consisting of alkyl, preferably $C_{1-20}$ alkyl; and aryl or heteroaryl, preferably phenyl, optionally substituted with one or more $C_{1-20}$ alkyl groups.

Substituted N, where present, may be —$NR^9$— wherein $R^9$ is as described above.

Preferably, each $R^3$, where present, is independently selected from $C_{1-40}$ hydrocarbyl, and is more preferably selected from $C_{1-20}$ alkyl; unsubstituted phenyl; phenyl substituted with one or more $C_{1-20}$ alkyl groups; a linear or branched chain of phenyl groups, wherein each phenyl may be unsubstituted or substituted with one or more substituents; and a crosslinkable group.

If n is 1 then exemplary repeat units of formula (III) include the following:

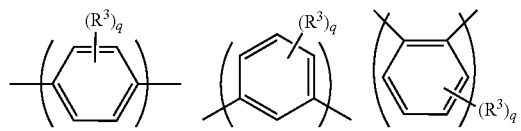

A particularly preferred repeat unit of formula (III) has formula (IIIa):

Substituents $R^3$ of formula (IIIa) are adjacent to linking positions of the repeat unit, which may cause steric hindrance between the repeat unit of formula (IIIa) and adjacent repeat units, resulting in the repeat unit of formula (IIIa) twisting out of plane relative to one or both adjacent repeat units.

Exemplary repeat units where n is 2 or 3 include the following:

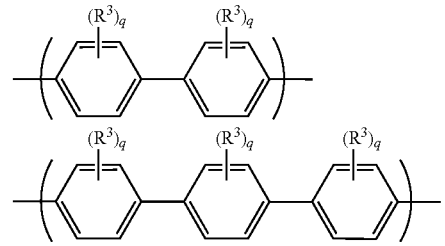

A preferred repeat unit has formula (IIIb):

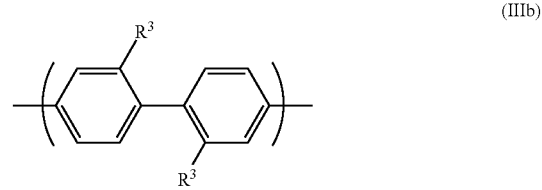

The two $R^3$ groups of formula (IIIb) may cause steric hindrance between the phenyl rings they are bound to, resulting in twisting of the two phenyl rings relative to one another.

A further class of arylene repeat units are optionally substituted fluorene repeat units, such as repeat units of formula (IV):

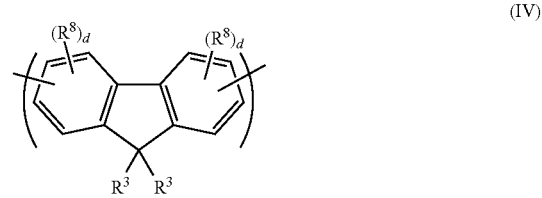

wherein $R^3$ in each occurrence is the same or different and is a substituent as described with reference to formula (III), and wherein the two groups $R^3$ may be linked to form a ring; $R^8$ is a substituent; and d is 0, 1, 2 or 3.

The aromatic carbon atoms of the fluorene repeat unit may be unsubstituted, or may be substituted with one or more substituents $R^8$. Exemplary substituents $R^8$ are alkyl, for example $C_{1-20}$ alkyl, wherein one or more non-adjacent C atoms may be replaced with O, S, NH or substituted N, C=O and —COO—, optionally substituted aryl, optionally substituted heteroaryl, alkoxy, alkylthio, fluorine, cyano and arylalkyl. Particularly preferred substituents include $C_{1-20}$ alkyl and substituted or unsubstituted aryl, for example phenyl. Optional substituents for the aryl include one or more $C_{1-20}$ alkyl groups.

Substituted N, where present, may be —$NR^5$— wherein $R^5$ is $C_{1-20}$ alkyl; unsubstituted phenyl; or phenyl substituted with one or more $C_{1-20}$ alkyl groups.

The extent of conjugation of repeat units of formula (IV) to aryl or heteroaryl groups of adjacent repeat units may be controlled by (a) linking the repeat unit through the 3- and/or 6-positions to limit the extent of conjugation across the repeat unit, and/or (b) substituting the repeat unit with one or more substituents $R^8$ in or more positions adjacent to the linking positions in order to create a twist with the adjacent repeat unit or units, for example a 2,7-linked fluorene carrying a $C_{1-20}$ alkyl substituent in one or both of the 3- and 6-positions.

The repeat unit of formula (IV) may be an optionally substituted 2,7-linked repeat unit of formula (IVa):

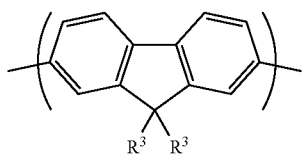

(IVa)

Optionally, the repeat unit of formula (IVa) is not substituted in a position adjacent to the 2- or 7-position. Linkage through the 2- and 7-positions and absence of substituents adjacent to these linking positions provides a repeat unit that is capable of providing a relatively high degree of conjugation across the repeat unit.

The repeat unit of formula (IV) may be an optionally substituted 3,6-linked repeat unit of formula (IVb)

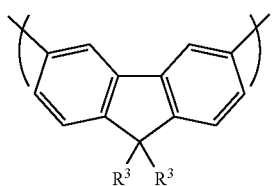

(IVb)

The extent of conjugation across a repeat unit of formula (IVb) may be relatively low as compared to a repeat unit of formula (IVa).

Another exemplary arylene repeat unit has formula (V):

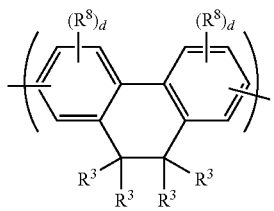

(V)

wherein $R^3$, $R^8$ and d are as described with reference to formula (III) and (IV) above. Any of the $R^3$ groups may be linked to any other of the $R^3$ groups to form a ring. Aromatic carbon atoms of the repeat unit of formula (V) may be unsubstituted, or may be substituted with one or more substituents.

Repeat units of formula (V) may have formula (Va) or (Vb):

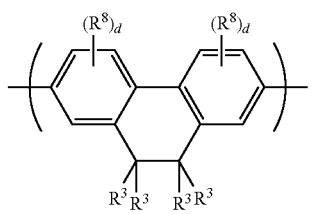

(Va)

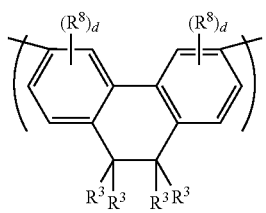

(Vb)

Further arylene co-repeat units include: phenanthrene repeat units; naphthalene repeat units; anthracene repeat units; and perylene repeat units. Each of these arylene repeat units may be linked to adjacent repeat units through any two of the aromatic carbon atoms of these units. Specific exemplary linkages include 9,10-anthracene; 2,6-anthracene; 1,4-naphthalene; 2,6-naphthalene; 2,7-phenanthrene; and 2,5-perylene. Each of these repeat units may be substituted or unsubstituted, for example substituted with one or more $C_{1-40}$ hydrocarbyl groups.

The polymer preferably contains one or more charge-transporting repeat units. Exemplary charge-transporting repeat units include repeat units of materials disclosed in, for example, Shirota and Kageyama, Chem. Rev. 2007, 107, 953-1010

Exemplary hole transporting repeat units may be repeat units of materials having a electron affinity of 2.9 eV or lower and an ionisation potential of 5.8 eV or lower, preferably 5.7 eV or lower.

Preferred hole-transporting repeat units are (hetero) arylamine repeat units, including repeat units of formula (VII):

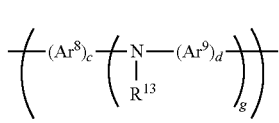

(VII)

wherein $Ar^8$ and $Ar^9$ in each occurrence are independently selected from substituted or unsubstituted aryl or heteroaryl, g is greater than or equal to 1, preferably 1 or 2, $R^{13}$ is H or a substituent, preferably a substituent, and c and d are each independently 1, 2 or 3.

$R^{13}$, which may be the same or different in each occurrence when g>1, is preferably selected from the group consisting of alkyl, for example $C_{1-20}$ alkyl, $Ar^{10}$, a branched or linear chain of $Ar^{10}$ groups, or a crosslinkable unit that is bound directly to the N atom of formula (VIII) or spaced apart therefrom by a spacer group, wherein $Ar^{10}$ in each occurrence is independently optionally substituted aryl or heteroaryl. Exemplary spacer groups are $C_{1-20}$ alkyl, phenyl and phenyl-$C_{1-20}$ alkyl.

Any of Ar⁸, Ar⁹ and, if present, Ar¹⁰ in the repeat unit of Formula (IX) may be linked by a direct bond or a divalent linking atom or group to another of Ar⁸, Ar⁹ and Ar¹⁰. Preferred divalent linking atoms and groups include O, S; substituted N; and substituted C.

Any of Ar⁸, Ar⁹ and, if present, Ar¹⁰ may be substituted with one or more substituents. Exemplary substituents are substituents R¹⁰, wherein each R¹⁰ may independently be selected from the group consisting of:

- substituted or unsubstituted alkyl, optionally $C_{1-20}$ alkyl, wherein one or more non-adjacent C atoms may be replaced with optionally substituted aryl or heteroaryl, O, S, substituted N, C=O or —COO— and one or more H atoms may be replaced with F; and
- a crosslinkable group attached directly to the fluorene unit or spaced apart therefrom by a spacer group, for example a group comprising a double bond such and a vinyl or acrylate group, or a benzocyclobutane group Preferred repeat units of formula (VII) have formulae 1-3:

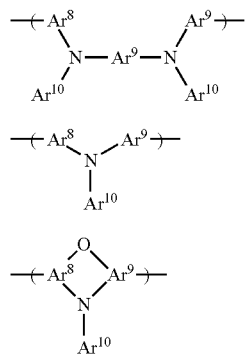

In one preferred arrangement, R¹³ is Ar¹⁰ and each of Ar⁸, Ar⁹ and Ar¹⁰ are independently and optionally substituted with one or more $C_{1-20}$ alkyl groups. Ar⁸, Ar⁹ and Ar¹⁰ are preferably phenyl.

In another preferred arrangement, the central Ar⁹ group of formula (I) linked to two N atoms is a polycyclic aromatic that may be unsubstituted or substituted with one or more substituents R¹⁰. Exemplary polycyclic aromatic groups are naphthalene, perylene, anthracene and fluorene.

In another preferred arrangement, Ar⁸ and Ar⁹ are phenyl, each of which may be substituted with one or more $C_{1-20}$ alkyl groups, and R¹³ is —(Ar¹⁰)$_r$ wherein r is at least 2 and wherein the group —(Ar¹⁰)$_r$ forms a linear or branched chain of aromatic or heteroaromatic groups, for example 3,5-diphenylbenzene wherein each phenyl may be substituted with one or more $C_{1-20}$ alkyl groups. In another preferred arrangement, c, d and g are each 1 and Ar⁸ and Ar⁹ are phenyl linked by an oxygen atom to form a phenoxazine ring.

Amine repeat units may be provided in a molar amount in the range of about 0.5 mol % up to about 50 mol %, optionally about 1-25 mol %, optionally about 1-10 mol %.

The polymer may contain one, two or more different repeat units of formula (VII).

Amine repeat units may provide hole-transporting and/or light-emitting functionality. Preferred fluorescent light-emitting amine repeat units include a blue light-emitting repeat unit of formula (VIIa) and a green light-emitting repeat unit formula (VIIb):

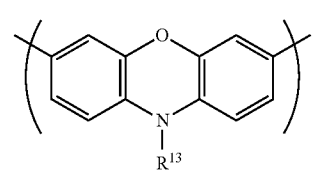

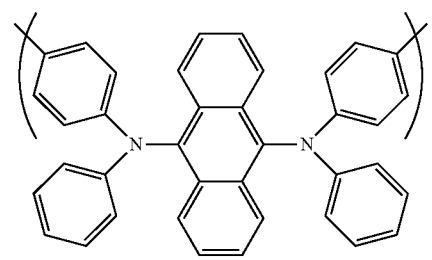

R¹³ of formula (VIIa) is preferably a hydrocarbyl, preferably $C_{1-20}$ alkyl, phenyl that is unsubstituted or substituted with one or more $C_{1-20}$ alkyl groups, or a branched or linear chain of phenyl groups wherein each said phenyl group is unsubstituted or substituted with one or more $C_{1-20}$ alkyl groups.

The repeat unit of formula (VIIb) may be unsubstituted or one or more of the rings of the repeat unit of formula (VIIb) may be substituted with one or more substituents R¹⁵, preferably one or more $C_{1-20}$ alkyl groups.

Another preferred charge-transporting repeat unit has formula (VIII):

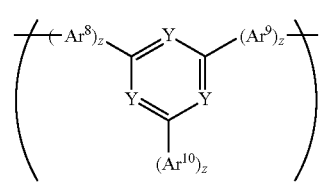

wherein Ar⁸, Ar⁹ and Ar¹⁰ are as described with reference to formula (VII) above, and may each independently be substituted with one or more substituents described with reference to Ar⁸, Ar⁹ and Ar¹⁰, and z in each occurrence is independently at least 1, optionally 1, 2 or 3, preferably 1, and Y is N or CR¹⁴, wherein R¹⁴ is H or a substituent, preferably H or $C_{1-10}$ alkyl. Preferably, Ar⁸, Ar⁹ and Ar¹⁰ of formula (VIII) are each phenyl, each phenyl being optionally and independently substituted with one or more $C_{1-20}$ alkyl groups.

In one preferred embodiment, all 3 groups Y are N.

If all 3 groups Y are CR¹⁴ then at least one of Ar⁸, Ar⁹ and Ar¹⁰ is preferably a heteroaromatic group comprising N.

Each of Ar⁸, Ar⁹ and Ar¹⁰ may independently be substituted with one or more substituents. In one arrangement, Ar⁸, Ar⁹ and Ar¹⁰ are phenyl in each occurrence. Exemplary substituents include R⁵ as described above with reference to formula (V), for example $C_{1-20}$ alkyl or alkoxy.

Ar¹⁰ of formula (VIII) is preferably phenyl, and is optionally substituted with one or more $C_{1-20}$ alkyl groups or a crosslinkable unit.

Preferably, z is 1 and each of Ar⁸, Ar⁹ and Ar¹⁰ is unsubstituted phenyl or phenyl substituted with one or more $C_{1-20}$ alkyl groups.

A particularly preferred repeat unit of formula (VIII) has formula (VIIIa), which may be unsubstituted or substituted with one or more substituents $R^5$, preferably one or more $C_{1-20}$ alkyl groups:

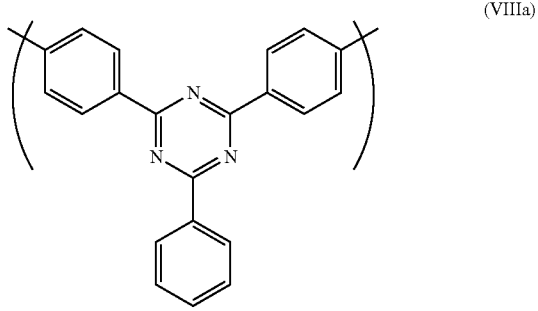

(VIIIa)

Light-Emitting Layers

An OLED may contain one or more light-emitting layers. A light-emitting layer may contain a polymer comprising repeat units of formula (I).

Suitable light-emitting materials for a light-emitting layer include polymeric, small molecule and dendritic light-emitting materials, each of which may be fluorescent or phosphorescent.

A light-emitting layer of an OLED may be unpatterned, or may be patterned to form discrete pixels. Each pixel may be further divided into subpixels. The light-emitting layer may contain a single light-emitting material, for example for a monochrome display or other monochrome device, or may contain materials emitting different colours, in particular red, green and blue light-emitting materials for a full-colour display.

A light-emitting layer may contain a mixture of more than one light-emitting material, for example a mixture of light-emitting materials that together provide white light emission.

A white-emitting OLED may contain a single, white-emitting layer or may contain two or more layers that emit different colours which, in combination, produce white light. The light emitted from a white-emitting OLED may have CIE x coordinate equivalent to that emitted by a black body at a temperature in the range of 2500-9000K and a CIE y coordinate within 0.05 or 0.025 of the CIE y co-ordinate of said light emitted by a black body, optionally a CIE x coordinate equivalent to that emitted by a black body at a temperature in the range of 2700-6000K.

Exemplary fluorescent polymeric light-emitting materials include polymers comprising one or more of arylene repeat units, arylene vinylene repeat units and arylamine repeat units.

Exemplary phosphorescent light-emitting materials include metal complexes. A phosphorescent material may be a material comprising a substituted or unsubstituted complex of formula (IX):

(IX)

wherein M is a metal; each of $L^1$, $L^2$ and $L^3$ is a coordinating group; q is a positive integer; r and s are each independently 0 or a positive integer; and the sum of (a.q)+(b.r)+(c.s) is equal to the number of coordination sites available on M, wherein a is the number of coordination sites on $L^1$, b is the number of coordination sites on $L^2$ and c is the number of coordination sites on $L^3$.

Heavy elements M induce strong spin-orbit coupling to allow rapid intersystem crossing and emission from triplet or higher states. Suitable heavy metals M include d-block metals, in particular those in rows 2 and 3 i.e. elements 39 to 48 and 72 to 80, in particular ruthenium, rhodium, palladium, rhenium, osmium, iridium, platinum and gold. Iridium is particularly preferred.

Exemplary ligands $L^1$, $L^2$ and $L^3$ include carbon or nitrogen donors such as porphyrin or bidentate ligands of formula (X):

(X)

wherein $Ar^5$ and $Ar^6$ may be the same or different and are independently selected from substituted or unsubstituted aryl or heteroaryl; $X^1$ and $Y^1$ may be the same or different and are independently selected from carbon or nitrogen; and $Ar^5$ and $Ar^6$ may be fused together. Ligands wherein $X^1$ is carbon and $Y^1$ is nitrogen are preferred, in particular ligands in which $Ar^5$ is a single ring or fused heteroaromatic of N and C atoms only, for example pyridyl or isoquinoline, and $Ar^6$ is a single ring or fused aromatic, for example phenyl or naphthyl.

To achieve red emission, $Ar^5$ may be selected from phenyl, fluorene, naphthyl and $Ar^6$ are selected from quinoline, isoquinoline, thiophene and benzothiophene.

To achieve green emission, $Ar^5$ may be selected from phenyl or fluorene and $Ar^6$ may be pyridine.

To achieve blue emission, $Ar^5$ may be selected from phenyl and $Ar^6$ may be selected from imidazole, pyrazole, triazole and tetrazole.

Examples of bidentate ligands are illustrated below:

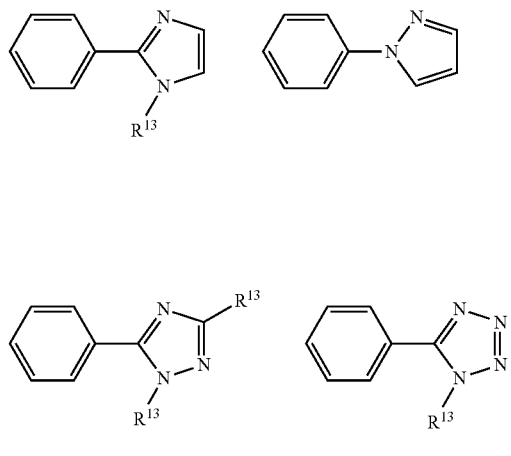

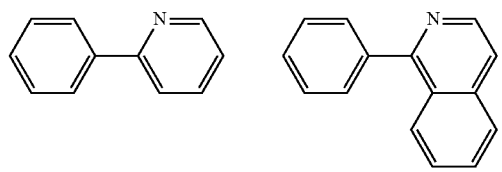

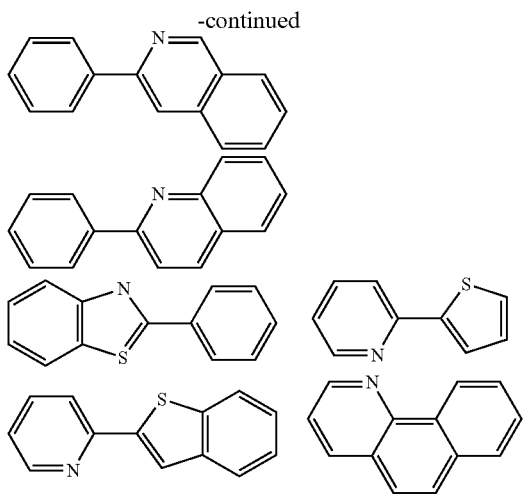

Each of Ar[5] and Ar[6] may carry one or more substituents. Two or more of these substituents may be linked to form a ring, for example an aromatic ring.

Other ligands suitable for use with d-block elements include diketonates, in particular acetylacetonate (acac), tetrakis-(pyrazol-1-yl)borate, 2-carboxypyridyl, triarylphosphines and pyridine, each of which may be substituted.

Exemplary substituents include groups $R^{13}$ as described above with reference to Formula (VII). Particularly preferred substituents include fluorine or trifluoromethyl which may be used to blue-shift the emission of the complex, for example as disclosed in WO 02/45466, WO 02/44189, US 2002-117662 and US 2002-182441; alkyl or alkoxy groups, for example $C_{1-20}$ alkyl or alkoxy, which may be as disclosed in JP 2002-324679; carbazole which may be used to assist hole transport to the complex when used as an emissive material, for example as disclosed in WO 02/81448; and dendrons which may be used to obtain or enhance solution processability of the metal complex, for example as disclosed in WO 02/66552.

A light-emitting dendrimer typically comprises a light-emitting core bound to one or more dendrons, wherein each dendron comprises a branching point and two or more dendritic branches. Preferably, the dendron is at least partially conjugated, and at least one of the branching points and dendritic branches comprises an aryl or heteroaryl group, for example a phenyl group. In one arrangement, the branching point group and the branching groups are all phenyl, and each phenyl may independently be substituted with one or more substituents, for example alkyl or alkoxy.

A dendron may have optionally substituted formula (XI)

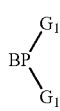

(XI)

wherein BP represents a branching point for attachment to a core and $G_1$ represents first generation branching groups.

The dendron may be a first, second, third or higher generation dendron. $G_1$ may be substituted with two or more second generation branching groups $G_2$, and so on, as in optionally substituted formula (XIa):

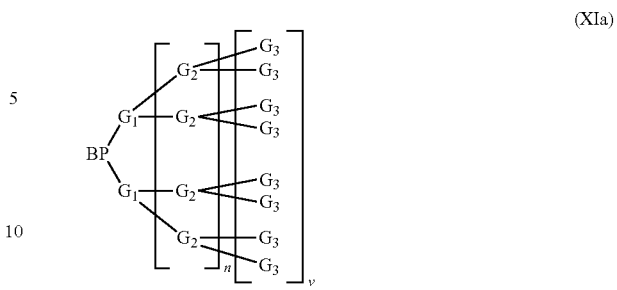

wherein u is 0 or 1; v is 0 if u is 0 or may be 0 or 1 if u is 1; BP represents a branching point for attachment to a core and $G_1$, $G_2$ and $G_3$ represent first, second and third generation dendron branching groups. In one preferred embodiment, each of BP and $G_1$, $G_2$ . . . $G_n$ is phenyl, and each phenyl BP, $G_1$, $G_2$ . . . $G_{n-1}$ is a 3,5-linked phenyl.

A preferred dendron is a substituted or unsubstituted dendron of formula (XIb):

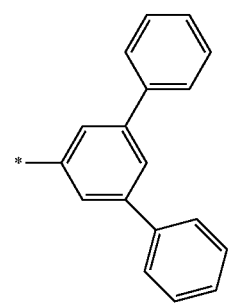

wherein * represents an attachment point of the dendron to a core.

BP and/or any group G may be substituted with one or more substituents, for example one or more $C_{1-20}$ alkyl or alkoxy groups.

Phosphorescent light-emitting materials may be provided in a light-emitting layer with a host material. The host material may be a host polymer of the invention.

The phosphorescent light-emitting material may be physically mixed with the host polymer or may be covalently bound thereto. The phosphorescent light-emitting material may be provided in a side-chain, main chain or end-group of the polymer. Where the phosphorescent material is provided in a polymer side-chain, the phosphorescent material may be directly bound to the backbone of the polymer or spaced apart therefrom by a spacer group, for example a $C_{1-20}$ alkyl spacer group in which one or more non-adjacent C atoms may be replaced by O or S. It will therefore be appreciated that a composition of the present invention may consist of or may comprise a polymer of the invention comprising repeat units of formula (I) with a phosphorescent light-emitting material bound to the polymer.

In the case where one or more phosphorescent light-emitting materials are mixed with a host material, the phosphorescent light-emitting material(s) may make up about 0.05 wt % up to about 50 wt %, optionally about 1-40 wt % of a host/phosphorescent light-emitting material composition.

In the case where one or more phosphorescent light-emitting materials are bound to a host material, for example a host polymer, the phosphorescent light-emitting material(s) may make up about 0.01-25 mol % of the material.

Charge Transporting and Charge Blocking Layers

In the case of an OLED, a hole transporting layer may be provided between the anode and the light-emitting layer or layers. Likewise, an electron transporting layer may be provided between the cathode and the light-emitting layer or layers.

Similarly, an electron blocking layer may be provided between the anode and the light-emitting layer and a hole blocking layer may be provided between the cathode and the light-emitting layer. Transporting and blocking layers may be used in combination. Depending on its HOMO and LUMO levels, a single layer may both transport one of holes and electrons and block the other of holes and electrons.

A charge-transporting layer or charge-blocking layer may be crosslinked, particularly if a layer overlying that charge-transporting or charge-blocking layer is deposited from a solution. The crosslinkable group used for this crosslinking may be a crosslinkable group comprising a reactive double bond such and a vinyl or acrylate group, or a benzocyclobutane group.

If present, a hole transporting layer located between the anode and the light-emitting layers preferably has a HOMO level of less than or equal to 5.5 eV, more preferably around 4.8-5.5 eV or 5.1-5.3 eV as measured by cyclic voltammetry. The HOMO level of the hole transport layer may be selected so as to be within 0.2 eV, optionally within 0.1 eV, of an adjacent layer (such as a light-emitting layer) in order to provide a small barrier to hole transport between these layers.

If present, an electron transporting layer located between the light-emitting layers and cathode preferably has a LUMO level of around 2.5-3.5 eV as measured by cyclic voltammetry. For example, a layer of a silicon monoxide or silicon dioxide or other thin dielectric layer having thickness in the range of 0.2-2 nm may be provided between the light-emitting layer nearest the cathode and the cathode. HOMO and LUMO levels may be measured using cyclic voltammetry.

A hole transporting layer may contain a homopolymer or copolymer comprising a repeat unit of formula (VII) as described above, for example a copolymer comprising one or more amine repeat units of formula (VII) and one or more arylene repeat units, for example one or more arylene repeat units selected from formulae (III), (IV) and (V).

An electron transporting layer may contain a polymer comprising a chain of optionally substituted arylene repeat units, such as a chain of fluorene repeat units.

If a hole- or electron-transporting layer is adjacent a light-emitting layer containing a phosphorescent material then the $T_1$ energy level of the material or materials of that layer are preferably higher than that of the phosphorescent emitter in the adjacent light-emitting layer.

Hole Injection Layers

A conductive hole injection layer, which may be formed from a conductive organic or inorganic material, may be provided between the anode 101 and the light-emitting layer 103 of an OLED as illustrated in FIG. 1 to assist hole injection from the anode into the layer or layers of semiconducting polymer. Examples of doped organic hole injection materials include optionally substituted, doped poly (ethylene dioxythiophene) (PEDT), in particular PEDT doped with a charge-balancing polyacid such as polystyrene sulfonate (PSS) as disclosed in EP 0901176 and EP 0947123, polyacrylic acid or a fluorinated sulfonic acid, for example Nafion®; polyaniline as disclosed in U.S. Pat. No. 5,723,873 and U.S. Pat. No. 5,798,170; and optionally substituted polythiophene or poly(thienothiophene). Examples of conductive inorganic materials include transition metal oxides such as VOx, MoOx and RuOx as disclosed in Journal of Physics D: Applied Physics (1996), 29(11), 2750-2753.

Cathode

The cathode 105 is selected from materials that have a workfunction allowing injection of electrons into the light-emitting layer of the OLED. Other factors influence the selection of the cathode such as the possibility of adverse interactions between the cathode and the light-emitting material. The cathode may consist of a single material such as a layer of aluminum. Alternatively, it may comprise a plurality of conductive materials such as metals, for example a bilayer of a low workfunction material and a high workfunction material such as calcium and aluminum, for example as disclosed in WO 98/10621. The cathode may comprise elemental barium, for example as disclosed in WO 98/57381, Appl. Phys. Lett. 2002, 81(4), 634 and WO 02/84759. The cathode may comprise a thin (e.g. 1-5 nm) layer of metal compound, in particular an oxide or fluoride of an alkali or alkali earth metal, between the organic layers of the device and one or more conductive cathode layers to assist electron injection, for example lithium fluoride as disclosed in WO 00/48258; barium fluoride as disclosed in Appl. Phys. Lett. 2001, 79(5), 2001; and barium oxide. In order to provide efficient injection of electrons into the device, the cathode preferably has a workfunction of less than 3.5 eV, more preferably less than 3.2 eV, most preferably less than 3 eV. Work functions of metals can be found in, for example, Michaelson, J. Appl. Phys. 48(11), 4729, 1977.

The cathode may be opaque or transparent. Transparent cathodes are particularly advantageous for active matrix devices because emission through a transparent anode in such devices is at least partially blocked by drive circuitry located underneath the emissive pixels. A transparent cathode comprises a layer of an electron injecting material that is sufficiently thin to be transparent. Typically, the lateral conductivity of this layer will be low as a result of its thinness. In this case, the layer of electron injecting material is used in combination with a thicker layer of transparent conducting material such as indium tin oxide.

It will be appreciated that a transparent cathode device need not have a transparent anode (unless, of course, a fully transparent device is desired), and so the transparent anode used for bottom-emitting devices may be replaced or supplemented with a layer of reflective material such as a layer of aluminum. Examples of transparent cathode devices are disclosed in, for example, GB 2348316.

Encapsulation

Organic optoelectronic devices tend to be sensitive to moisture and oxygen. Accordingly, the substrate preferably has good barrier properties for prevention of ingress of moisture and oxygen into the device. The substrate is commonly glass, however alternative substrates may be used, in particular where flexibility of the device is desirable. For example, the substrate may comprise one or more plastic layers, for example a substrate of alternating plastic and dielectric barrier layers or a laminate of thin glass and plastic.

The device may be encapsulated with an encapsulant (not shown) to prevent ingress of moisture and oxygen. Suitable encapsulants include a sheet of glass, films having suitable barrier properties such as silicon dioxide, silicon monoxide, silicon nitride or alternating stacks of polymer and dielectric or an airtight container. In the case of a transparent cathode device, a transparent encapsulating layer such as silicon monoxide or silicon dioxide may be deposited to micron levels of thickness, although in one preferred embodiment the thickness of such a layer is in the range of 20-300 nm. A getter material for absorption of any atmospheric moisture and/or oxygen that may permeate through the substrate or encapsulant may be disposed between the substrate and the encapsulant.

Formulation Processing

A formulation suitable for forming a charge-transporting or light-emitting layer may be formed from the polymer of the invention, any further components of the layer such as light-emitting dopants, and one or more suitable solvents.

The formulation may be a solution of the polymer and any other components in the one or more solvents, or may be a dispersion in the one or more solvents in which one or more components are not dissolved. Preferably, the formulation is a solution.

Solvents suitable for dissolving semiconducting polymers, particularly polymers comprising alkyl substituents, include benzenes substituted with one or more $C_{1-10}$ alkyl or $C_{1-10}$ alkoxy groups, for example toluene, xylenes and methylanisoles.

A charge-transporting or light-emitting layer of an OLED may be formed by depositing the formulation containing a polymer as described herein and evaporating the one or more solvents.

Particularly preferred solution deposition techniques including printing and coating techniques such spin-coating and inkjet printing.

Spin-coating is particularly suitable for devices wherein patterning of the light-emitting layer is unnecessary—for example for lighting applications or simple monochrome segmented displays.

Inkjet printing is particularly suitable for high information content displays, in particular full colour displays. A device may be inkjet printed by providing a patterned layer over the first electrode and defining wells for printing of one colour (in the case of a monochrome device) or multiple colours (in the case of a multicolour, in particular full colour device). The patterned layer is typically a layer of photoresist that is patterned to define wells as described in, for example, EP 0880303.

As an alternative to wells, the ink may be printed into channels defined within a patterned layer. In particular, the photoresist may be patterned to form channels which, unlike wells, extend over a plurality of pixels and which may be closed or open at the channel ends.

Other solution deposition techniques include dip-coating, roll printing and screen printing.

EXAMPLES

Synthesis of Monomer Example 1

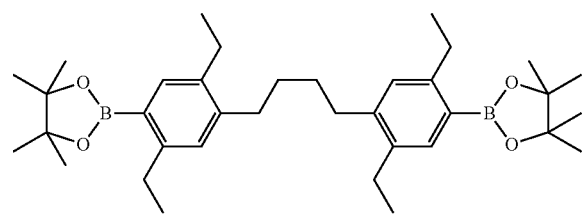

Stage 1

An oven-dried 3 L 4-neck flask fitted with an internal thermometer, N2 bubbler, overhead stirrer and oven-dried mL pressure-equalising dropping funnel was charged with 1,4-dibromo-2,5-diethylbenzene (70 g, 240 mmol) and dry THF (700 mL). The solution was cooled with stirring to <−70° C. to produce a white slurry. s-Butyllithium (335 mL, 1.4 M, 465 mmol) was charged to the dropping funnel and added dropwise over the space of 1.5 h ensuring the reaction temperature did not exceed −70° C. The slurry was stirred for 3 h after which GCMS confirmed the lithiation was complete. The dropping funnel was charged with a solution of 1,4-diiodobutane (13.8 mL, 105 mmol) in dry THF (140 mL) which was then added dropwise over 0.75 h. The resulting slurry was allowed to warm to room temperature and stirred for 12 h. The reaction was quenched by addition of water. The mixture was transferred to a separating funnel and the layers were separated. The aqueous layer was extracted with diethyl ether and the combined organics were washed with water, dried with MgSO$_4$, filtered and concentrated to yield an orange oil. The product was triturated with 500 mL methanol for 0.5 h and filtered as a white solid before being recrystallised from toluene/IPA to yield a white powder that was dried in the oven (24.21 g, 48%). GCMS indicated a purity of ~96% and the material was taken to the next stage without further purification Stage 2

An oven-dried 2 L 4-neck flask fitted with an internal thermometer, N2 bubbler, overhead stirrer and oven-dried mL pressure-equalising dropping funnel was charged with Stage 1 material (45 g, 94 mmol) and dry THF (450 mL). The solution was cooled with stirring to <−70° C. to produce a white slurry. n-Butyllithium (96 mL, 2.5 M, 225 mmol) was charged to the dropping funnel and added dropwise over the space of 0.75 h ensuring the reaction temperature did not exceed −70° C. The slurry was stirred for 5 h after which GCMS confirmed the lithiation was complete. The dropping funnel was charged with a solution of IPPB (50 mL, 235 mmol) in dry THF (100 mL) which was then added dropwise over 0.75 h. The resulting slurry was allowed to warm to room temperature and stirred for 12 h. The reaction was quenched by addition of HCl in ether. The solvent was removed, diethyl ether added, the mixture was transferred to a separating funnel and the layers were separated. The aqueous layer was extracted with diethyl ether and the combined organics were washed with water, dried with MgSO$_4$, filtered and concentrated to yield an orange oil. The product was triturated with 500 mL acetonitrile for 1 h in an ice-bath and filtered as a white solid before being recrystallised from acetonitrile to yield a white powder. The solid was dissolved in a 2:1 (v/v) mixture of DCM and hexanes and passed through a plug of Florisil® (diameter 11 cm, height 4 cm) on silica (diameter 11 cm, height 7 cm) and then recrystallised from acetonitrile three times to give a white powder which was filtered and dried in the oven (13 g, 24%). HPLC indicated a purity of 99.67%

$^1$H NMR (referenced to CDCl$_3$ peak at 7.26 ppm): 7.57 (2H, s), 6.98 (2H, s), 2.84-2.88 (4H, m), 2.61-2.64 (8H, m), 1.67 (4H, m), 1.32 (24H, s), 1.17-1.21 (12H, m)

Synthesis of Monomer Example 2

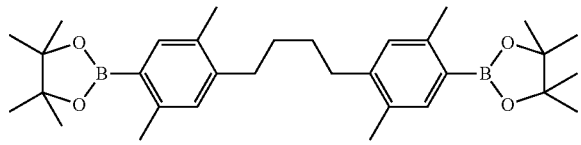

Stage 1

An oven-dried 3 L 4-neck flask fitted with an internal thermometer, N2 bubbler, overhead stirrer and oven-dried pressure-equalising dropping funnel was charged with 1,4-dibromo-2,5-dimethylbenzene (70 g, 265 mmol) and dry THF (700 mL). The solution was cooled with stirring to <−70° C. to produce a white slurry. s-Butyllithium (370 mL, 1.4 M, 518 mmol) was charged to the dropping funnel and added dropwise over the space of 2 h ensuring the reaction temperature did not exceed −70° C. The slurry was stirred for 2 h after which GCMS confirmed the lithiation was complete. The dropping funnel was charged with a solution of 1,4-diiodobutane (15.7 mL, 119 mmol) in dry THF (160 mL) which was then added dropwise over 0.75 h. The resulting pale yellow slurry was allowed to warm to room temperature and stirred for 12 h. The reaction was quenched by addition of water. The mixture was transferred to a separating funnel and the layers were separated. The aqueous layer was extracted with diethyl ether and the combined organics were washed with water, dried with MgSO$_4$, filtered and concentrated to yield an off-white solid. The product was triturated with 300 mL methanol for 2 h and recrystallised from toluene/IPA to yield a white powder that was dried in the oven (31.86 g, 63%). GCMS indicated a purity of ~96% and the material was taken to the next stage without further purification

Stage 2

An oven-dried 2 L 4-neck flask fitted with an internal thermometer, N2 bubbler, overhead stirrer and oven-dried pressure-equalising dropping funnel was charged with Stage 1 material (31.5 g, 74 mmol) and dry THF (350 mL). The solution was cooled with stirring to <−70° C. to produce a white slurry. n-Butyllithium (62 mL, 2.5 M, 155 mmol) was charged to the dropping funnel and added dropwise over the space of 0.5 h ensuring the reaction temperature did not exceed −70° C. The slurry was stirred for 4.5 h. The dropping funnel was charged with a solution of iPPB (33 mL, 161 mmol) in dry THF (60 mL) which was then added dropwise over 0.5 h. The resulting slurry was allowed to warm to room temperature and stirred for 12 h. The reaction was quenched by addition of HCL in ether. The THF was removed, diethyl ether added, the mixture was transferred to a separating funnel and the layers were separated. The aqueous layer was extracted with diethyl ether and the combined organics were washed with water, dried with MgSO$_4$, filtered and concentrated to yield a white solid. The product was triturated with 500 mL methanol for 0.5 h. The filtered solid was purified by chromatography on silica using a gradient of DCM in hexanes as the eluant. The product-containing fractions were concentrated and recrystallised from acetonitrile to yield a white powder that was dried in the oven (20.44 g, 53%). HPLC indicated the purity was 99.77%

$^1$H NMR (referenced to CDCl$_3$ peak at 7.26 ppm): 7.53 (2H, s), 6.93 (2H, s), 2.59 (4H, m), 2.47 (6H, s), 2.26 (6H, s), 1.62 (4H, m), 1.33 (24H, s)

Host Polymer Examples

Polymers were prepared by Suzuki polymerisation as described in WO 00/53656 of a polymerisation mixture containing the molar percentages of monomers given in Table 1.

TABLE 1

| Polymer | Diester monomer (mol %) | Dihalo monomers (mol %) | Viscosity average molecular weight (Mz) | Weight average molecular weight (Mw) | Peak average molecular weight (Mp) | Number average molecular weight (Mn) | Pd |
|---|---|---|---|---|---|---|---|
| Polymer Example 1 | Monomer Example 1 (50) | 3 (5) 4 (45) | 1,280,000 | 630,000 | 770,000 | 21,000 | 30.00 |
| Polymer Example 2 | Monomer Example 2 (50) | 3 (9) 4 (41) | 111,000 | 64,000 | 71,000 | 15,000 | 4.16 |
| Comparative Polymer 1 | Comparative Monomer 1 (50) | 6 (50) | 455,000 | 256,000 | 224,000 | 96,000 | 2.78 |
| Comparative Polymer 2 | Monomer 7 (50) | Comparative Monomer 2 (50) | 571,000 | 235,000 | 177,000 | 17,600 | 13.40 |
| Comparative Polymer 3 | 7 (50) | 6 (28.5) 3 (21.5) | | | | | |
| Polymer Example 3 | Monomer Example 1 (50) | 4 (25) 3 (25) | | | | | |
| Polymer Example 4 | Monomer Example 1 (50) | 4 (10) 3 (40) | | | | | |
| Polymer Example 5 | Monomer Example 1 (50) | 4 (35) 10 (15) | | | | | |
| Polymer Example 6 | Monomer Example 1 (50) | 4 (30) 11 (20) | | | | | |

TABLE 1-continued

| Polymer | Diester monomer (mol %) | Dihalo monomers (mol %) | Viscosity average molecular weight (Mz) | Weight average molecular weight (Mw) | Peak average molecular weight (Mp) | Number average molecular weight (Mn) | Pd |
|---|---|---|---|---|---|---|---|
| Polymer Example 7 | Monomer Example 1 (50) | 4 (32) 12 (18) | | | | | |
| Polymer Example 8 | Monomer Example 1 (50) | 4 (32) 13 (18) | | | | | |
| Comparative Polymer 4 | 9 (50) | 3 (5) 4 (45) | | | | | |

Monomer 1 (Monomer Example 1)

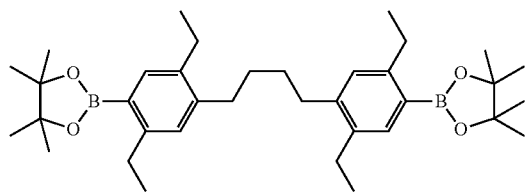

Monomer 2 (Monomer Example 2)

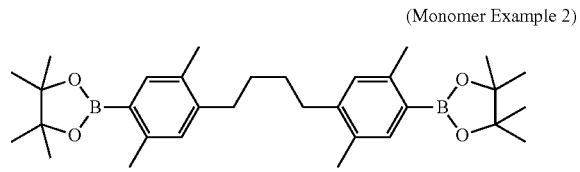

Monomer 3

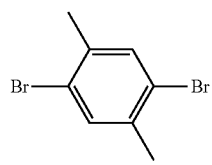

Monomer 4

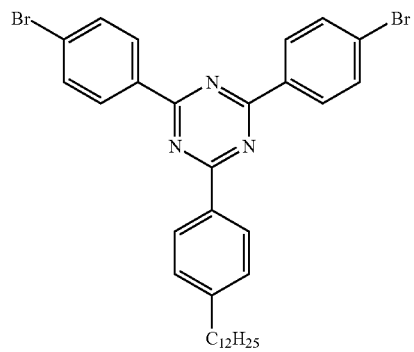

Monomer 5 (Comparative Monomer 1)

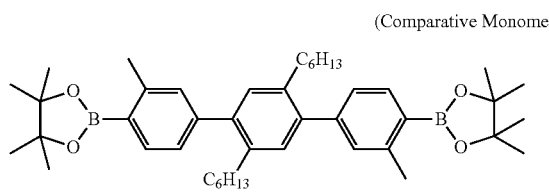

Monomer 6

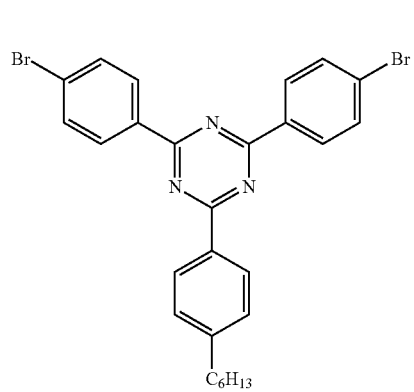

Monomer 7

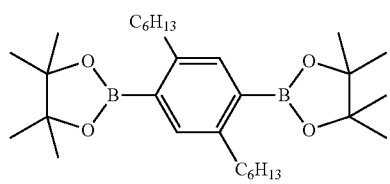

Monomer 8
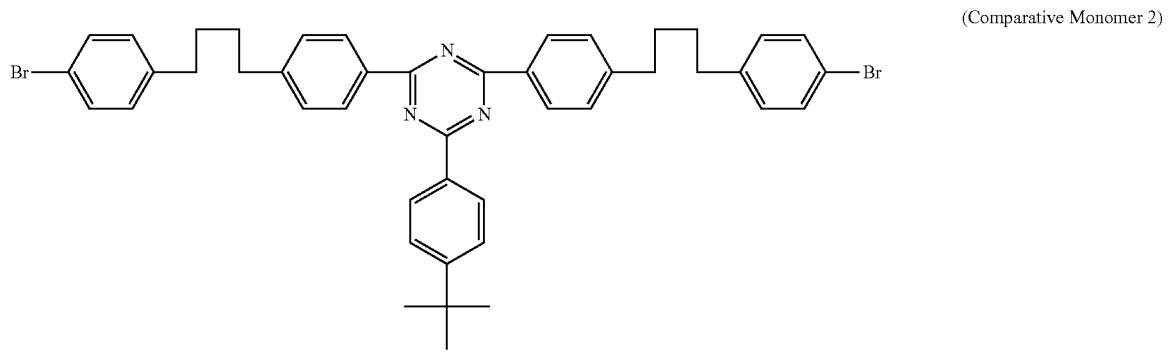
(Comparative Monomer 2)
Monomer 9
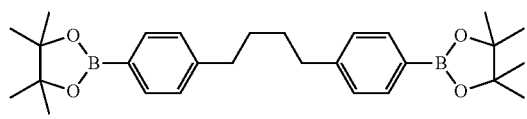
(Comparative Monomer 3)
Monomer 10
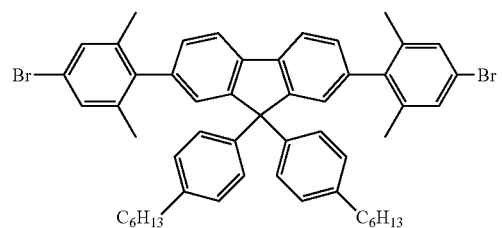
Monomer 11
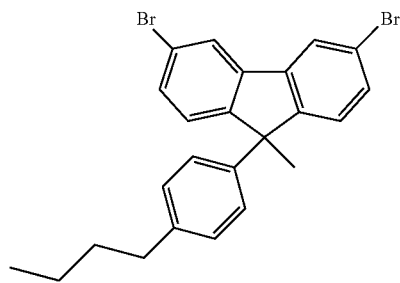
Monomer 12
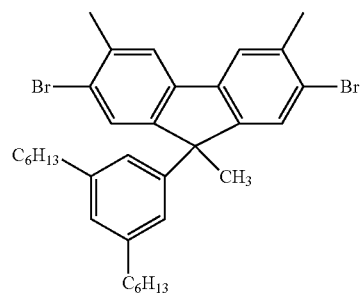
Monomer 13
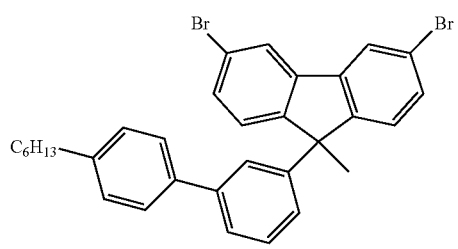

Monomer 12 is described in JP2012-137538. Monomer 10 is described in JP2012-137537.
Polymer Example 1 includes the following repeating structures:
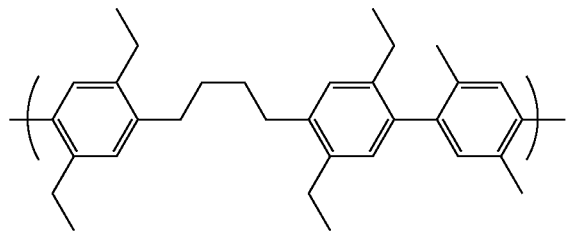
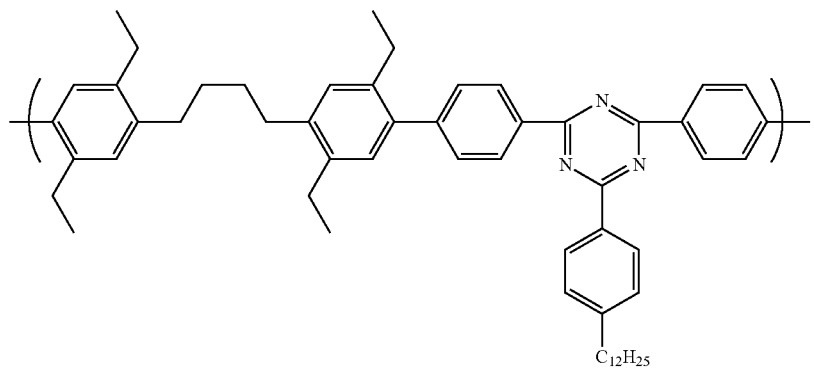
Polymer Example 2 includes the following repeating structures:
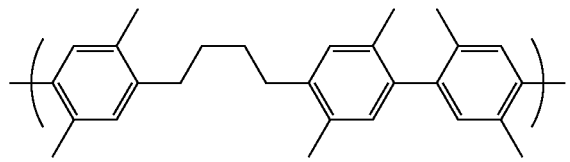
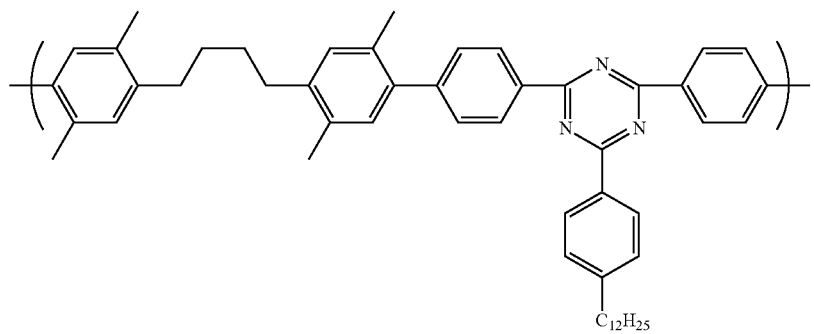

Comparative Polymer 1 includes the following repeating structure:

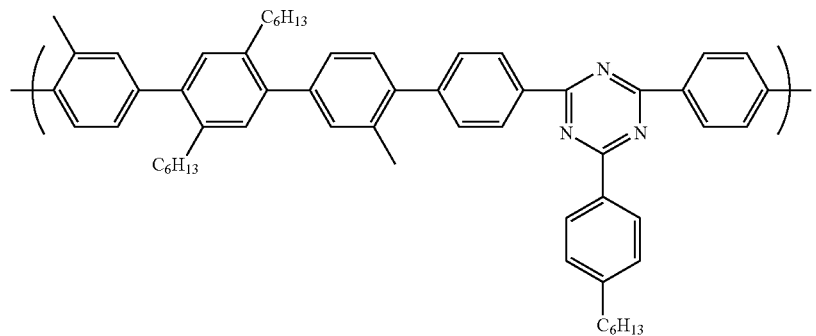

Monomer 8 (Comparative Monomer 2) was prepared as described in WO 2011/141714. Comparative Polymer 2 includes the following repeating structure:

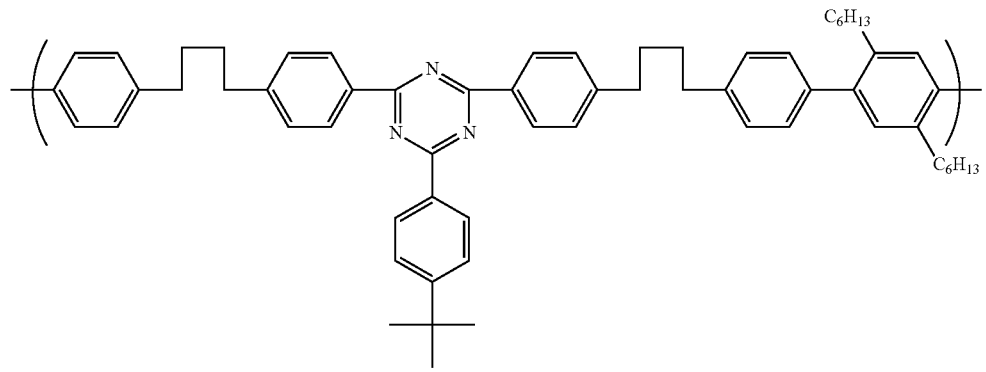

Comparative Polymer 3 includes the following repeating structures:

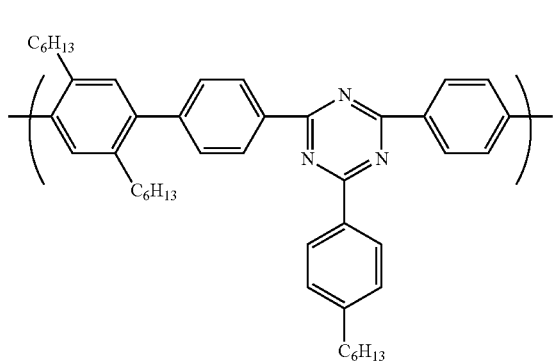

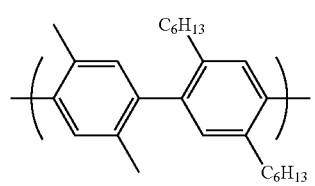

Comparative Polymer 4 includes the following repeating structures:

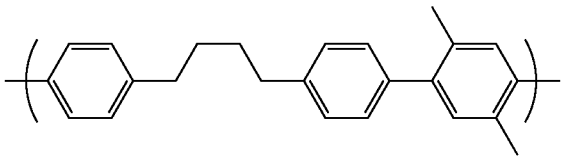

Composition Examples

A composition of 95 mol % of a polymer as described above and 5 mol % of Blue Phosphorescent Emitter 1, illustrated below, was dissolved in o-xylene and cast as a film by spin-coating.

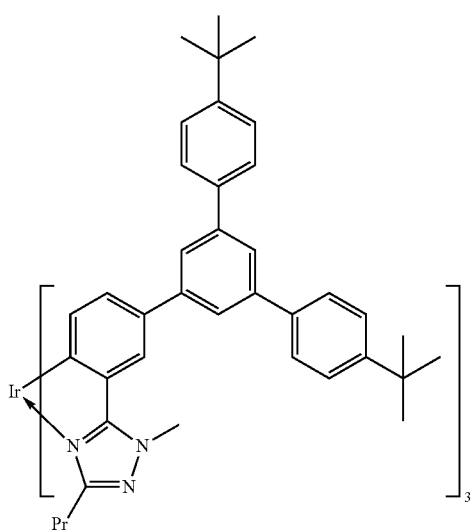

Blue Phosphorescent Emitter 1

The core of Blue Phosphorescent Emitter 1 is disclosed in WO2004/101707. Formation of dendrons is described in WO 02/066552.

Synthesis of Blue Phosphorescent Emitter 1
Stage 1:

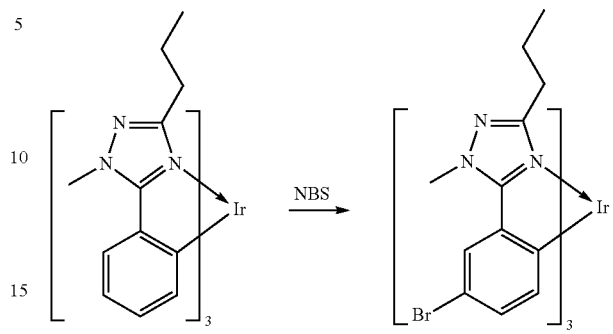

fac-Tris(1-methyl-5-phenyl-3-propyl-[1,2,4]triazolyl) iridium-(III) (1.1 g) (Shih-Chun Lo et al., *Chem. Mater.* 2006, 18, 5119-5129) (1.1 g) was dissolved in DCM (100 mL) under a flow of nitrogen. N-Bromosuccinimide (0.93 g) was added as a solid and the mixture was stirred at room temperature with protection from light. After 24 h HPLC analysis showed ~94% product and ~6% dibromide intermediate.

A further 50 mg of NBS was added and stirring continued for 16 hours. A further 50 mg of NBS was added and stirring continued for 24 h. HPLC indicated over 99% product. Warm water was added and stirred for 0.5 h. The layers were separated and the organic layer passed through a plug of celite eluting with DCM. The filtrate was concentrated to ~15 mL and hexane was added to the DCM solution to precipitate the product as a yellow solid in 80% yield.

Stage 2:

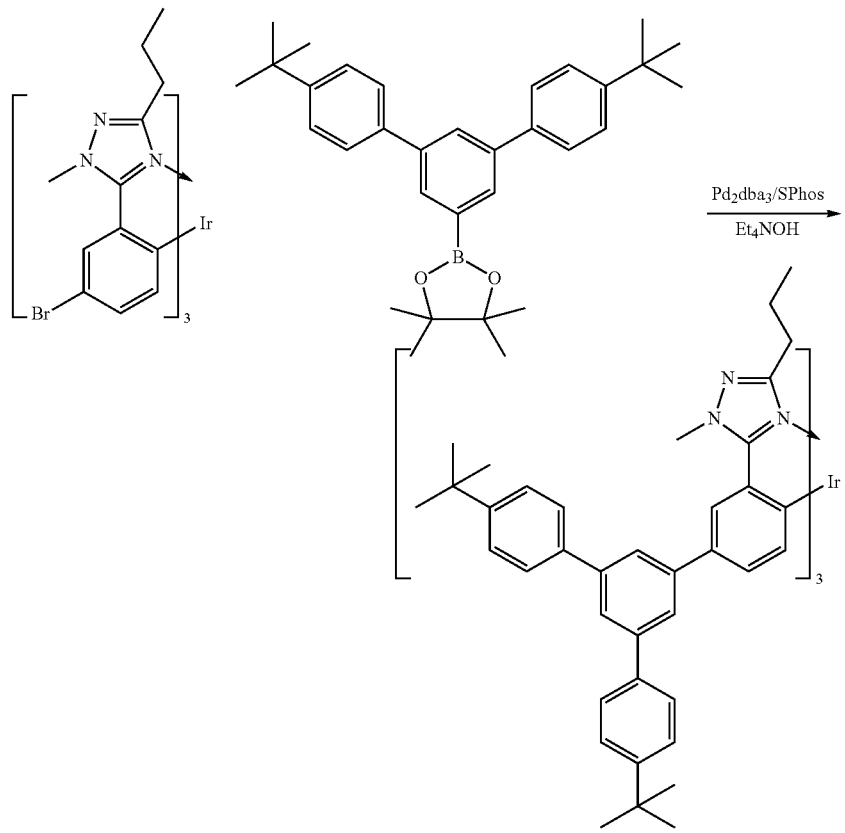

Stage 1 material (8.50 g) and 3,5-bis(4-tert-butylphenyl)phenyl-1-boronic acid pinacol ester (15.50 g) were dissolved in toluene (230 mL). The solution was purged with nitrogen for 1 h before 2-dicyclohexylphosphino-2',6'-dimethoxybiphenyl (66 mg) and tris(dibenzylidene)dipalladium (75 mg) were added using 10 mL of nitrogen-purged toluene. A 20 wt % solution of tetraethylammonium hydroxide in water (60 mL) was added in one portion and the mixture as stirred for 20 h with the heating bath set to 105° C. T.L.C. analysis indicated all the stage material had been consumed and only one fluorescent spot was observed. The reaction mixture was cooled and filtered into a separating funnel. The layers were separated and the aqueous layer extracted with toluene. The organic extracts were washed with water, dried with magnesium sulphate, filtered and concentrated to yield the crude product as a yellow/orange solid. Pure compound was obtained by column chromatography eluting with a gradient of ethyl acetate in hexanes followed by precipitation from DCM/methanol. HPLC indicated a purity of 99.75% and a yield of 80% (11.32 g). 1H NMR (referenced to CDCl3): 7.83 (3H, d), 7.76 (6H, s), 7.73 (3H, s) 7.63 (12H, d) 7.49 (12H, d), 7.21 (3H, dd), 6.88 (3H, d), 4.28 (9H, s), 2.25 (3H, m), 1.98 (3H, m), 1.4-1.5 (57H, m), 1.23 (3H, m), 0.74 (9H, t)

With reference to Table 2, it can be seen that photoluminescent quantum yield (PLQY) of the films are comparable for compositions containing Polymer Example 1 and Comparative Polymer 2, whereas the PLQY values of compositions containing Comparative Polymers 1 and 3 are much lower. Without wishing to be bound by any theory, it is believed that the extended conjugation between adjacent phenyl groups in the backbones of Comparative Polymers 1, 3 and 4 results in a low triplet energy level and quenching of phosphorescence.

TABLE 2

| Polymer | PLQY (%) | CIE x | CIE y |
|---|---|---|---|
| Polymer Example 1 | 63 | 0.158 | 0.308 |
| Comparative Polymer 1 | 7 | 0.189 | 0.173 |
| Comparative Polymer 2 | 76 | 0.157 | 0.299 |
| Comparative Polymer 3 | 15 | 0.177 | 0.307 |
| Comparative Polymer 4 | 6 | 0.156 | 0.302 |

Green Device Examples

Organic light-emitting devices having the following structure were prepared:
ITO/HIL/HTL/LE/Cathode
wherein ITO is an indium-tin oxide anode; HIL is a hole-injecting layer; HTL is a hole-transporting layer; LE is a light-emitting layer; and the cathode comprises a layer of metal fluoride in contact with the light-emitting layer and a layer of aluminum formed over the layer of metal fluoride.

To form the device, a substrate carrying ITO was cleaned using UV/Ozone. The hole injection layer was formed by spin-coating an aqueous formulation of a hole-injection material available from Plextronics, Inc. A hole transporting layer was formed to a thickness of 20 nm by spin-coating Hole-Transporting Polymer 1 and crosslinking the polymer by heating. A light-emitting layer was formed by depositing a light-emitting composition of a host polymer (65 wt %) and Green Phosphorescent Emitter 1, illustrated below (35 wt %), by spin-coating from o-xylene solution a thickness of 75 nm. Green Phosphorescent Emitter 1 is a dendrimeric phosphorescent emitter, as described in WO 02/066552. A cathode was formed by evaporation of a first layer of a metal fluoride to a thickness of about 2 nm, a second layer of aluminum to a thickness of about 200 nm and a third layer of silver.

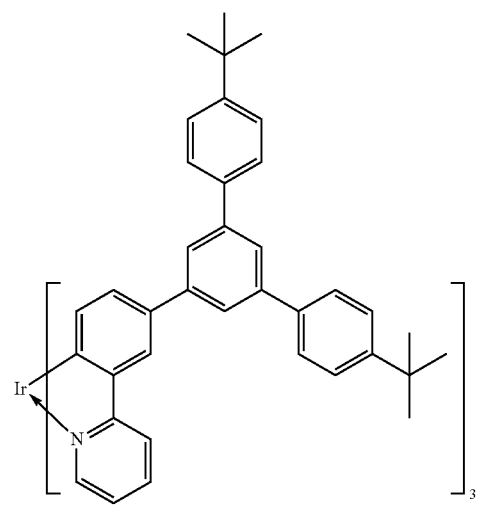

Green Phosphorescent Emitter 1

Hole-Transporting Polymer 1 was formed by Suzuki polymerisation as described in WO 00/53656 of the following monomers:

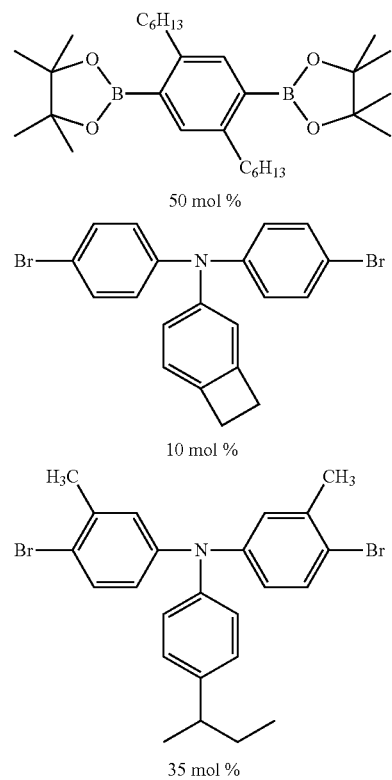

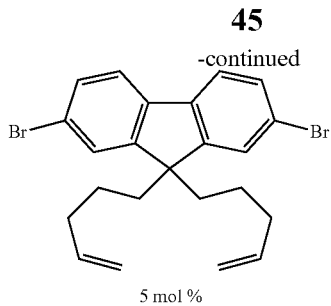

5 mol %

With reference to Table 3, it can be seen that devices containing Polymer Examples 1 and 2 as host polymer both reach a brightness of 1000 cd/m² at a lower voltage; have higher conductivity as shown by the voltage required to reach a current of 10 mA/cm²; and are more efficient than a device containing Comparative Polymer 2 as host polymer.

Performance of devices containing Polymer Examples 1 and 2 is comparable to performance of the device containing Comparative Polymer 3.

TABLE 3

| Polymer | V at 1 kcd/m² | J at 1 kcd/m² | V at 10 mA/cm² | Efficiency Lm/W at 1 kcd/m² | Efficiency Cd/A at 1 kcd/m2 | EQE at 1 kcd/m² (%) | Max EQE (%) |
|---|---|---|---|---|---|---|---|
| Polymer Example 1 | 4.75 | 1.3 | 6.78 | 49.16 | 74.63 | 20.68 | 21.31 |
| Polymer Example 2 | 4.45 | 1.4 | 6.48 | 50.59 | 72.48 | 20.02 | 20.52 |
| Comparative Polymer 2 | 5.46 | 1.6 | 7.37 | 36.12 | 62.5 | 17.39 | 17.58 |
| Comparative Polymer 3 | 4.44 | 1.4 | 6.19 | 50.93 | 71.85 | 19.8 | 20.68 |

The time taken for brightness of these devices to fall to 70% (T70) and to 50% (T50) of a starting luminance of 5,000 cd/m² is shown in Table 4. Polymer Examples 1 and 2 both have higher lifetimes than Comparative Polymer 2. The lifetime of Comparative Polymer 3 is slightly higher than Polymer Examples 1 or 2, but this polymer gives poor efficiency when used with a blue phosphorescent emitter, as shown in Table 2 above.

TABLE 4

| Host polymer | T70 (hours) | T50 (hours) | J (mA/cm²) |
|---|---|---|---|
| Comparative Polymer 2 | 2.67 | 10.31 | 7.63 |
| Polymer Example 1 | 5.12 | 21.80 | 7.08 |
| Polymer Example 2 | 4.81 | 24.96 | 6.77 |
| Comparative Polymer 3 | 6.33 | 30.17 | 6.99 |

Blue Device Example 1

A device was prepared as described for the green device examples above except that the light-emitting layer was formed by spin-coating a mixture of Polymer Example 1 and Blue Phosphorescent Emitter 1 (36 mol %)

Comparative Blue Device 1

A device was prepared as described in Blue Device Example 1, except that Polymer Example 1 was replaced with Comparative Polymer 2.

Blue Device Example 2

A device containing a light-emitting layer of a mixture of Polymer Example 1 and Blue Phosphorescent Emitter 1 (36 wt %) was prepared as described for the green device examples above. The hole-transporting layer was formed by Suzuki polymerization of the following monomers, as described in WO 00/53656:

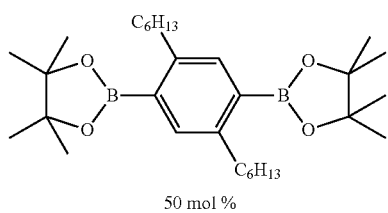

50 mol %

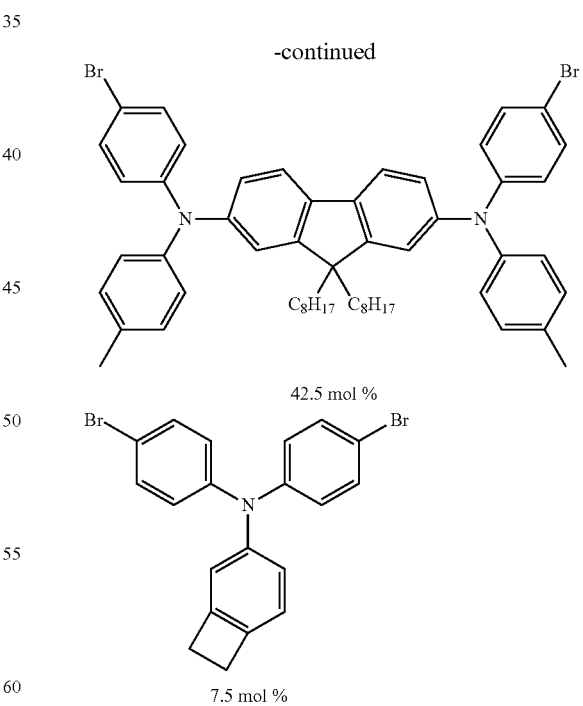

42.5 mol %

7.5 mol %

Comparative Blue Device 2

A device was prepared as described in Blue Device Example 2, except that Polymer Example 1 was replaced with Comparative Polymer 2.

Data for blue devices are provided in Table 5, in which T70 and T50 are the time taken for luminance to fall to 70% and 50% respectively of a starting luminance.

TABLE 5

| Device | V at 1000 cd/m² | J (mA/cm²) at 1000 cd/m2 | V at 10 mA/cm² | Eff. (Lm/W) at 1 kcd/m2 | Eff. (Cd/A) at 1 kcd/m2 | EQE at 1 kcd/m² (%) | Max EQE (%) | T70 (hours) | T50 (hours) |
|---|---|---|---|---|---|---|---|---|---|
| Comparative Blue Device 1 | 6.34 | 3.2 | 7.61 | 15.38 | 31.02 | 17.52 | 19.04 | 2.05 | 8.41 |
| Blue Device Example 1 | 6.11 | 3.6 | 7.28 | 14.13 | 27.53 | 13.43 | 15.91 | 1.13 | 5.60 |
| Blue Device Example 2 | 5.79 | 7.8 | 6 | 6.98 | 12.88 | 5.86 | 6.14 | 14.52 | 36.66 |
| Comparative Blue Device 2 | 5.91 | 7.4 | 6.19 | 7.05 | 13.42 | 7.87 | 8.47 | 7.91 | 25.99 |

The polymers of the invention are more conductive than the comparative polymers, as is shown by the higher current density values for the inventive polymers.

White Devices—General Process

Organic light-emitting devices having the following structure were prepared:

ITO/HIL/HTL/LEL/Cathode wherein ITO is an indium-tin oxide anode; HIL is a hole-injecting layer comprising a hole-injecting material, HTL is a hole-transporting layer, and LEL is a light-emitting layer containing a metal complex and a host polymer and formed by spin-coating.

A substrate carrying ITO was cleaned using UV/Ozone. A hole injection layer was formed to a thickness of about 35 nm by spin-coating an aqueous formulation of a hole-injection material available from Plextronics, Inc. A hole transporting layer was formed to a thickness of about 22 nm by spin-coating Hole-Transporting Polymer 1 and crosslinking the polymer by heating. A light-emitting layer was formed by depositing a light-emitting composition containing a host polymer doped with red, green and blue light-emitting metal complexes to a thickness of about 75 nm by spin-coating. A cathode was formed by evaporation of a first layer of a sodium fluoride to a thickness of about 2 nm, a second layer of aluminum to a thickness of about 100 nm and a third layer of silver to a thickness of about 100 nm.

The blue light-emitting metal complex was complex selected from Blue Phosphorescent Emitter 1 and Blue Phosphorescent Emitter 2; the green emitting metal complex was Green Phosphorescent Emitter 1 described above; and the red-emitting metal complex was Red Phosphorescent Emitter 1, as described in WO/2012/153082.

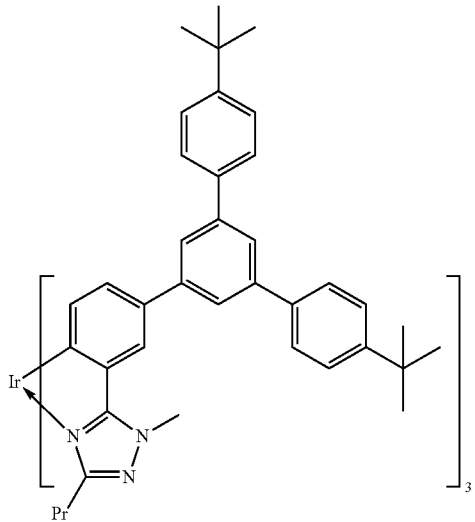

Blue Phosphorescent Emitter 1

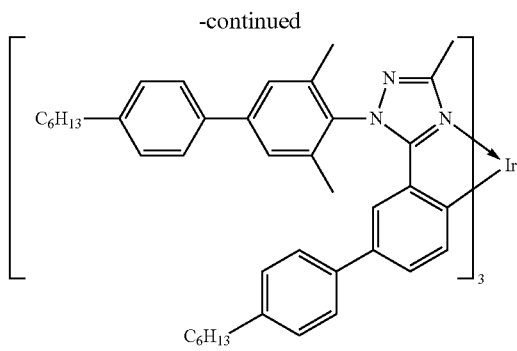

Blue Phosphorescent Emitter 2

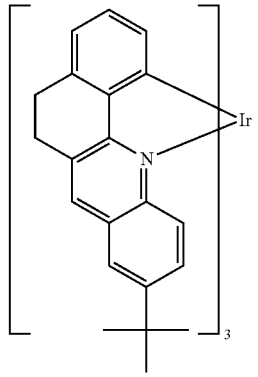

Red Phosphorescent Emitter 1

The composition of white device examples and comparative white devices is provided in Table 6.

TABLE 6

|  | Host polymer | Blue emitter | Light-emitting layer composition (wt %) | V at 1 kcd/m2 | J at 1 kcd/m2 | V at 10 mA/cm2 |
|---|---|---|---|---|---|---|
| White Device Example 1 | Polymer Example 3 | Blue 1 | 53:45:1:1 | 5.87 | 3.50 | 6.8 |
| Comparative White Device 1 | Comparative Polymer 2 | Blue 1 | 53:45:1:1 | 6.71 | 3.7 | 7.69 |
| White Device Example 2 | Polymer Example 3 | Blue 2 | 63:35:1:1 | 5.87 | 3.30 | 6.9 |
| Comparative White Device 2 | Comparative Polymer 2 | Blue 2 | 63:35:1:1 | 7.22 | 3.3 | 8.59 |

The light-emitting layer composition given in Table 6 is the Host Polymer:Blue Emitter:Green Emitter:Red Emitter ratio.

Table 6 shows that devices of the invention have higher conductivity than the comparative devices.

Hole-Transporting Polymer Examples

Hole-transporting polymers of the invention containing repeat units of formula (I) and hole-transporting amine repeat units, and comparative hole-transporting polymers, were prepared by Suzuki polymerisation as described in WO 00/53656 using monomers as shown in Table 7.

TABLE 7

| Polymer | Diester monomer (mol %) | Dihalo monomers (mol %) | Viscosity average molecular weight (Mz) | Weight average molecular weight (Mw) | Peak average molecular weight (Mp) | Number average molecular weight (Mn) | Pd |
|---|---|---|---|---|---|---|---|
| Polymer Example 10 | Monomer Example 1 (50) | 15 (42.5) 16 (7.5) | 498,000 | 243,000 | 243,000 | 16,000 | 14.83 |
| Comparative Polymer 10 | 7 (50) | 15 (42.5) 16 (7.5) | 403,000 | 224,000 | 215,000 | 43,000 | 5.22 |
| Polymer Example 11 | Monomer Example 1 (50) | 17 (42.5) 16 (7.5) | 367,000 | 187,000 | 182,000 | 108,000 | 9.08 |
| Comparative Polymer 11 | 7 (50) | 17 (40) 18 (5) 19 (5) | 352,000 | 147,000 | 118,000 | 15,000 | 10.08 |

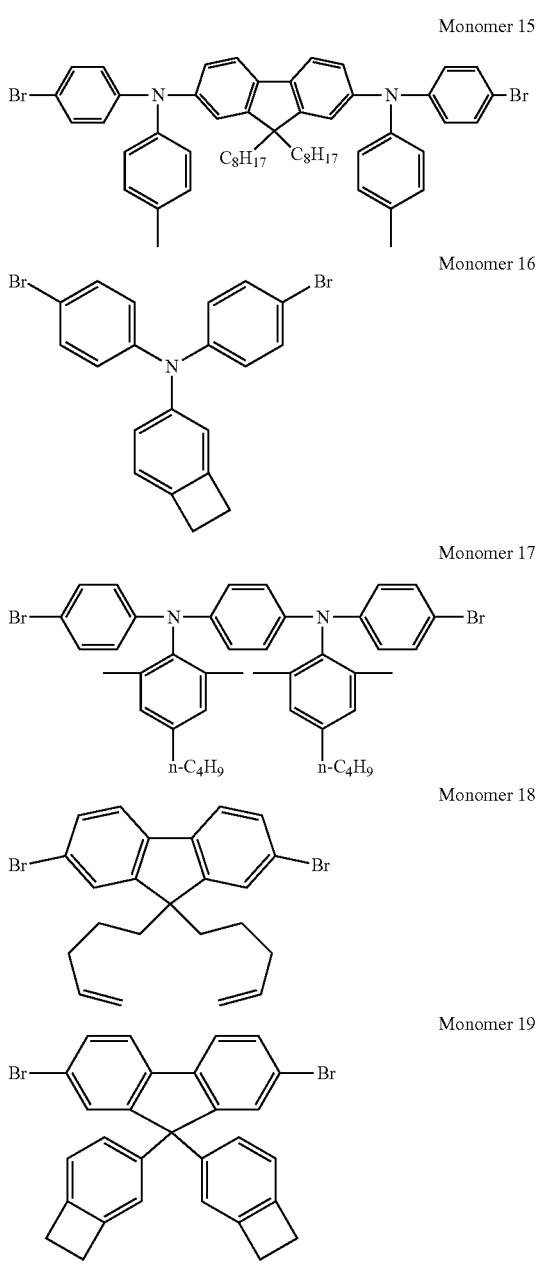

Energy Levels

Polymer Example 10 has a HOMO level of 5.14 eV and a LUMO level of about 1.9 eV as measured by cyclic voltammetry.

Polymer Example 11 has a HOMO level of 5.05 eV and a LUMO level of about 1.9 eV as measured by cyclic voltammetry.

Photoluminescence Measurements—Phosphorescent Green Blends

A 95:5 weight % composition of Polymer Example 10 and Green Phosphorescent Emitter 1 was dissolved in mixed xylenes and cast by spin-coating on a glass substrate. For the purpose of comparison, a comparative composition containing Comparative Polymer 10 in place of Polymer Example 10 was cast in the same way.

With reference to Table 8, photoluminescence quantum yield (PLQY) for the exemplary composition is much higher than that of the comparative composition, indicating that the exemplary polymer causes little or no quenching of phosphorescence of the green phosphorescent emitter. This indicates that the exemplary hole-transporting polymers may be used as hole-transporting materials of a hole-transporting layer without causing significant quenching of phosphorescence from an adjacent light-emitting layer.

TABLE 8

| Polymer | PLQY/% | CIE X | CIE Y |
|---|---|---|---|
| Comparative Polymer 10 | 48 | 0.296 | 0.629 |
| Polymer Example 10 | 74 | 0.291 | 0.635 |

Photoluminescence Measurements—Phosphorescent Blue Blends

A 95:5 weight % composition of Polymer Example 11 and Blue Phosphorescent Emitter 1 was dissolved in mixed xylenes and cast by spin-coating on a glass substrate. For the purpose of comparison, a comparative composition containing Comparative Polymer 11 in place of Polymer Example 11 was cast in the same way.

With reference to Table 9, photoluminescence quantum yield (PLQY) for the exemplary composition is much higher than that of the comparative composition, indicating that the exemplary polymer causes little or no quenching of phosphorescence of the blue phosphorescent emitter. This indicates that the exemplary hole-transporting polymers may be used as hole-transporting materials of a hole-transporting layer without causing significant quenching of phosphorescence from an adjacent light-emitting layer.

TABLE 9

| Polymer | PLQY/% | CIE X | CIE Y |
|---|---|---|---|
| Comparative Polymer 11 | 7 | 0.169 | 0.115 |
| Polymer Example 11 | 42 | 0.157 | 0.285 |

Blue Device Example 3

A blue light-emitting device was prepared as described for the Green Device Examples, except that the hole-transporting layer was formed by spin-coating and cross-linking Polymer Example 10 and the light-emitting layer was formed by spin-coating Polymer Example 1 (55 weight %) and Blue Phosphorescent Emitter 1 (45 weight %). The device emitted light having a peak at 473 nm.

Blue Device Example 4

A blue light-emitting device was prepared as described for the Blue Device Example 3, except that Polymer Example 11 was used to form the hole-transporting layer. The device emitted light having a peak at 476 nm.

Although the present invention has been described in terms of specific exemplary embodiments, it will be appreciated that various modifications, alterations and/or combinations of features disclosed herein will be apparent to those skilled in the art without departing from the scope of the invention as set forth in the following claims.

The invention claimed is:

1. A composition comprising a polymer and at least one light-emitting dopant, the polymer comprising repeat units of formula (I) and one or more co-repeat units:

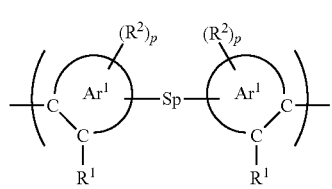

Ar¹ in each occurrence independently represents an aryl or heteroaryl group;
R¹ and R² are independently, in each occurrence, $C_{1-40}$ hydrocarbyl, $-OR^{11}$, $-SR^{11}$, $-N(R^{11})_2$, or $-Si(R^{11})_3$, wherein $R^{11}$ in each occurrence is a $C_{1-40}$ hydrocarbyl;
p independently in each occurrence is 0 or a positive integer;
Sp represents a $C_{1-20}$ alkyl chain spacer group wherein one or more non-adjacent C atoms of the chain may be replaced with O, S, $-NR^{11}$, $-Si(R^4)_2-$, $-C(=O)-$ or $-COO-$ and wherein $R^4$ in each occurrence is independently H or a $C_{1-40}$ hydrocarbyl group, with the proviso that Sp contains at least one sp³-hybridized carbon atom separating the two Ar¹ groups; and
each group Ar¹ is bound to an aromatic group of a co-repeat unit;
wherein the light-emitting dopant is a phosphorescent dopant having a photoluminescent spectrum with a peak in the range of 400-490 nm.

2. A composition according to claim 1 wherein Ar¹ is an aryl group and the Ar¹ groups may be the same or different.

3. A composition according to claim 2 wherein each Ar¹ is phenyl.

4. A composition according to claim 3 wherein the repeat unit of formula (I) has formula (Ia):

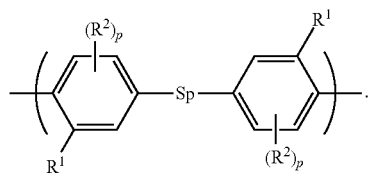

5. A composition according to claim 4 wherein the repeat unit of formula (I) has formula (Ib):

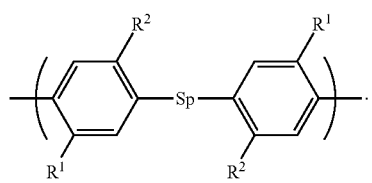

6. A composition according to claim 1 wherein R¹ in each occurrence is independently a $C_{1-20}$ alkyl.

7. A composition according to claim 1 wherein the one or more co-repeat units include a charge-transporting repeat unit.

8. A composition according to claim 7 wherein the charge-transporting repeat unit has formula (VII):

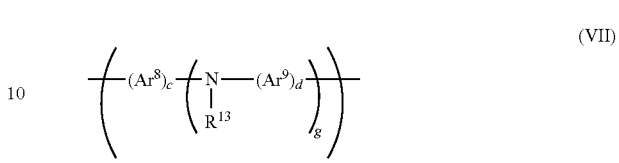

wherein Ar⁸ and Ar⁹ in each occurrence are independently substituted or unsubstituted aryl or heteroaryl, g is greater than or equal to 1, $R^{13}$ is H, $C_{1-20}$ alkyl, Ar¹⁰, a branched or linear chain of Ar¹⁰ groups, or a crosslinkable unit that is bound directly to the N atom of formula (VIII) or spaced apart therefrom by a spacer group, wherein Ar¹⁰ in each occurrence is independently an unsubstituted or substituted aryl or heteroaryl; c and d are each independently 1, 2 or 3; and any two of Ar⁸, Ar⁹ and $R^{13}$ directly linked to the same N atom may be linked by a direct bond or a divalent linking group.

9. A composition according to claim 7 wherein the charge-transporting repeat unit has formula (VIII):

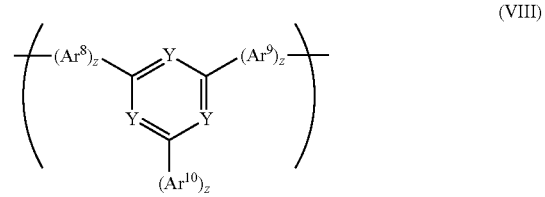

wherein Ar⁸, Ar⁹ and Ar¹⁰ are in each occurrence independently substituted or unsubstituted aryl or heteroaryl; z in each occurrence is independently at least 1, optionally 1, 2 or 3, preferably 1, and Y is N or $CR^{14}$, wherein $R^{14}$ is H or $C_{1-10}$ alkyl.

10. A formulation comprising a composition according to claim 1 and at least one solvent.

11. An organic light-emitting device comprising an anode, a cathode and one or more organic layers between the anode and cathode including a light-emitting layer wherein at least one of the one or more organic layers comprises a polymer according to claim 1.

12. An organic light-emitting device wherein the organic light-emitting layer comprises a composition according to claim 11.

13. An organic light-emitting device wherein the organic layers comprise a hole-transporting layer between the anode and the light-emitting layer, the hole-transporting layer comprising a polymer according to claim 12.

14. A method of forming an organic light-emitting device according to claim 12 comprising the step of forming the light-emitting layer over one of the anode and the cathode and forming the other of the anode and the cathode over the light-emitting layer.

15. A composition according to claim 1 wherein the phosphorescent dopant has a photoluminescent spectrum with a peak in the range of 420-490 nm.

* * * * *